United States Patent [19]

Yoshinaga et al.

[11] Patent Number: 5,049,664
[45] Date of Patent: Sep. 17, 1991

[54] TREHALOSE DERIVATIVES

[75] Inventors: Junji Yoshinaga, Neyagawa; Takeshi Shogaki, Suita; Takao Kakita, Toyanaka; Hiromi Ozeki, Osaka; Yoshiko Kato, Nishinomiya, all of Japan

[73] Assignee: Sawai Pharmaceutical Co., Ltd., Osaka, Japan

[21] Appl. No.: 394,714

[22] Filed: Aug. 16, 1989

[30] Foreign Application Priority Data

Aug. 26, 1988 [JP] Japan ................. 63-213307
Apr. 11, 1989 [JP] Japan ................... 1-92791

[51] Int. Cl.$^5$ ..................... C07H 13/00; C07H 15/00
[52] U.S. Cl. ................... 536/119; 536/4.1; 536/115; 536/120
[58] Field of Search ............ 536/119, 115, 120, 4.1

[56] References Cited

U.S. PATENT DOCUMENTS

| 4,243,663 | 3/1981 | Azuma, I et al. | |
| 4,307,229 | 12/1981 | Liav et al. | 536/119 |
| 4,612,304 | 9/1986 | Fukushi | 536/119 |
| 4,684,719 | 8/1987 | Nishikawa et al. | 536/119 |
| 4,720,456 | 1/1988 | Wagner et al. | 536/16.8 |
| 4,814,436 | 3/1989 | Shibata et al. | 536/119 |

FOREIGN PATENT DOCUMENTS

| 1202622 | 4/1986 | Canada | 536/119 |
| 2633690 | 2/1977 | Fed. Rep. of Germany . | |
| 3248167 | 12/1982 | Fed. Rep. of Germany . | |
| 58-185599 | 10/1983 | Japan | 536/119 |
| 59-46294 | 3/1984 | Japan . | |
| 59-157097 | 9/1984 | Japan | 536/119 |
| 59-181297 | 10/1984 | Japan | 536/119 |
| 61-130298 | 7/1986 | Japan . | |
| 61-289038 | 8/1986 | Japan . | |
| 62-72695 | 1/1987 | Japan . | |
| 62-53926 | 3/1987 | Japan . | |
| 62-50478 | 5/1987 | Japan . | |
| 62-174094 | 7/1987 | Japan . | |
| 62-56499 | 8/1987 | Japan . | |
| 62-59117 | 9/1987 | Japan . | |
| 62-19598 | 12/1987 | Japan . | |
| 2133399 | 7/1984 | United Kingdom | 536/119 |

Primary Examiner—Ronald W. Griffin
Assistant Examiner—Everett White
Attorney, Agent, or Firm—Scully, Scott, Murphy & Presser

[57] ABSTRACT

A trehalose derivative of the formula:

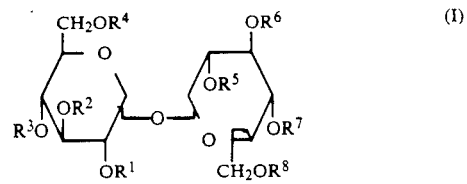

wherein one, two, three or four of $R^1$, $R^2$, $R^3$, $R^4$, $R^5$, $R^6$, $R^7$ and $R^8$ are independently selected from the group consisting of $C_{1-40}$ aliphatic acyl groups and all the rest of them are hydrogen atoms, with the proviso that:
 a) when one of them is $C_{1-40}$ aliphatic acyl group, then it is not 2-palmitoyl or 6-aliphatic acyl,
 b) when two of them are $C_{1-40}$ aliphatic acyl groups, then they are not located at corresponding positions with each other,
 c) when three of them are $C_{1-40}$ aliphatic acyl groups, then they are not 2,3,2'-tripalmitoyl, and
 d) when four of them are $C_{1-40}$ aliphatic acyl groups, then they are not located at corresponding positions with each other or at 2,3,4,2'- or 2,3,6,2'-positions.

The compounds of the above formula have anti-tumor activity.

19 Claims, No Drawings

TREHALOSE DERIVATIVES

BACKGROUND OF THE INVENTION

1. Field of the invention

The present invention relates to novel α,α-trehalose derivatives having anti-tumor activity.

2. Background information

Derivatives of α,α-trehalose, such as 6,6'-dimycolate of α,α-trehalose extracted from cell wall of a tubercle bacillus, have attracted considerable attention, as they have various immuno-pharmacological activities such as immunoadjuvant activity, ability of granuloma formation, ability of macrophage activation, ability of enhancing non-specific protection, anti-tumor activity, etc. [Yakugaku Zasshi, 107, 37–45 (1987) and Kekkaku, 63 (3), 41–54 (1988)]. Particular chemical structures of these liposaccharides, however, have not been well established due to the fact that their mycolic acid moieties, forming the most notable characteristic of cell walls of acid-fast bacteria, are long-chain fatty acid (having 60 to 88 carbon atoms) of extremely strong hydrophobic property and that they are unstable at elevated temperatures. In addition, these compounds are not appropriate for medical application because composition (such as number of carbon atoms, unsaturation and substitution) of their mycolic acid moieties varies from one bacterial species to another and thus products with uniform composition cannot be obtained. Furthermore, particularly the liposaccharides having mycolic acid moieties of 70 to 80 carbon atoms have fault that they are highly toxic.

Among other α,α-trehalose derivatives, there may be mentioned 2,3,6'-trimycolate of α,α-trehalose, obtained from *Rhodococcus aurantiacus*, which has very unusual unsymmetrical structure [FEBS letters, 203, 239–242 (1986)] and 2,6'-dimycolate of α,α-trehalose extracted from the same bacterium [60th Annual Meeting of Biochemical Society of Japan, Oct. 1987]. However, pharmacological activities of these unsymmetrical mycolic ester of α,α-trehalose have not been sufficiently clarified and neither structure nor composition of their mycolic acid moieties have been determined.

Other difatty-acid esters of α,α-trehalose have been described [U.S. Pat. No. 4,612,304; CA-A-1,202,622; JP-B-50478/1987; JP-A-46294/1984; JP-A-157097/1984; JP-A-289038/1986; JP-A-53926/1987; JP-A-174094/1987 and Chem. Pharm. Bull. 33, 4455 (1985)]. All these compounds are substituted with fatty acid residues at symmetrical (e.g.6,6')positions of α,α-trehalose.

Also, there have been known 2-palmitoyl, 2,2'-dipalmitoyl and 2,3,2'-tripalmitoyl derivatives of α,α-trehalose by J. Chem. Soc. Perkin I, 1980, 1940–1943, 6-(3-hydroxy-2-tetradecanyloctadecanoyl)ester by Carbohydrate Res., 125, 323–328 (1984), 6,6'-bis-(3-hydroxy-2-tetracosanylhydroxyhexacontanoyl)ester by Chem. Phys. Lipids, 16, 91–106 (1976), 2,6,6'-tris(3-acetoxy-2-tetracosanyl-methoxyhexacontanoyl)ester by Bull. Soc. Chim. France, 1478–1482 (1956), 2,3,4,2'-esters by DE-A1-3248167, 2,3,6,2'-esters by Chem. Phys. Lipids, 29 241–266 (1981), 4,6,4',6'-tetrastearoyl ester by Chem. Pharm. Bull. 30, 1169–1174 (1982) and 4,6,4', 6',-esters by JP-A-157097/1984.

After an extensive study on the synthesis of glycolipids having long chain aliphatic acyl group as their lipid moieties, the present inventors have successfully prepared α,α-trehalose derivatives having mycolic acid or aliphatic acid moieties of defined chemical structure, uniform constitution and thus improved safety, particularly unsymmetrical derivatives (i.e. compounds except those having only the same acyl groups located at paired positions designated by numbers corresponding with each other).

SUMMARY OF THE INVENTION

The present invention provides a trehalose derivative of the formula:

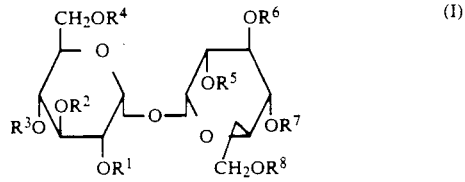

wherein one, two, three or four of $R^1$, $R^2$, $R^3$, $R^4$, $R^5$, $R^6$, $R^7$ and $R^8$ are independently selected from the group consisting of $C_{1\text{-}40}$ aliphatic acyl groups and all the rest of them are hydrogen atoms,
with the proviso that:
a) when one of them is $C_{1\text{-}40}$ aliphatic acyl group, then it is not 2-palmitoyl or 6-aliphatic acyl,
b) when two of them are $C_{1\text{-}40}$ aliphatic acyl groups, then they are not located at corresponding positions with each other,
c) when three of them are $C_{1\text{-}40}$ aliphatic acyl groups, then they are not 2,3,2'-tripalmitoyl, and
d) when four of them are $C_{1\text{-}40}$ aliphatic acyl groups, then they are not located at corresponding positions with each other or at 2,3,4,2'- or 2,3,6,2'-positions.

DETAILED DESCRIPTION OF THE INVENTION

Definitions

As used herein, the expression "$C_{1\text{-}40}$ aliphatic acyl group" refers to a group consisting of a carbonyl group and hydrogen atom or a saturated or unsaturated, straight or branched chain aliphatic hydrocarbon group combined with said carbonyl group, the total number of carbon atoms being 1 to 40, and preferably 6 to 36. When said aliphatic hydrocarbon group is a branched one, said branching may occur at any position such as α- or β-position to the carbonyl group but it is preferred that a side chain with a greater number of carbon atoms is present at α-position. The side chain may also be branched. In a preferred embodiment, the main and side chains have a backbone with up to 30 and preferably 5 to 25 or 5 to 20 carbon atoms. When said aliphatic hydrocarbon group is unsaturated, any number of, preferably 1 to 5 and e.g. 1,2 or 3 double or triple bond or a combination thereof may be present. In addition, said aliphatic hydrocarbon group may have one or more, preferably 1 to 5, e.g. 1,2 or 3 substituents which are independently selected from groups found in the naturally occurring mycolic acids, such as hydroxy, methoxy, epoxy, oxo, carboxy, methylene (forming cyclopropane ring) etc., and protected hydroxy or protected carboxy.

The term "hydroxy-protecting group" includes mono- and bi-valent groups which are used in the saccharide or peptide synthesis to temporarily replace the hydrogen atom of hydroxy group in order to avoid any possible undesirable reaction on the hydroxy group during a condensation reaction such as acylation and which can be easily removed after the condensation reaction.

Said monovalent hydroxy-protecting group includes α-aryl(lower)alkyl (e.g. benzyl, p-chlorobenzyl, diphenylmethyl, trityl etc., which are removable by catalytic hydrogenation, HBr/acetic acid or p-toluenesulfonic acid), trifluoro-, chloro-, methoxy- or aryloxy-acetyl (removable by base), (lower)alkoxycarbonyl (removable by alkali), 2-tetrahydropyranyl or 2-tetrahydrothiopyranyl (removable by acid), tri(lower)alkylsilyl (removable by water, acid or alkali), tri(lower)alkylmethyl (removable by HBr/trifluoro acetic acid), 1-(α-aryl(-lower)alkyloxycarbonylamino)-2,2,2,-trifluoroethyl (removable by catalytic hydrogenation or acid), 2-(α-aryl(lower)alkyloxycarbonyl)benzoyl (removable by catalytic hydrogenation or hydrazine), tri(lower)alkylmethyloxycarbonyl, arylcarbonyl(lower)alkylcarbonyl (removable by alkali) etc.

Said bivalent hydroxy-protecting group includes lower alkylidene which may be substituted with a substituent such as monocyclic aryl, lower alkoxy or oxo (said alkylidene group may form a cyclic group such as a cyclic acetal (e.g. in the case of methylene, ethylidene, benzylidene, isopropylidene, cyclohexylidene etc., which are removable by acid or catalytic hydrogenation), a cyclic ortho-ester (e.g. in the case of methoxymethylene, 1-ethoxyethylidene etc., which are removable by acid) or a cyclic ester (e.g. cyclic carbonic ester, removable by base), polysiloxanediyl (e.g. a group of the formula: -Si(lower alkyl)$_2$-O-Si(lower alkyl)$_2$-, removable by TBAF, acid or alkali) and the like.

The term "aryl" refers to a group comprising a small number of, and preferably one benzene ring which may be substituted with 1 to 5, preferably 1 to 3 substituents such as lower alkyl, lower alkoxy, halogen, nitro etc.

The term "lower alkyl" refers to a straight or branched chain alkyl having 1 to 8, preferably 1 to 6 and particularly 1 to 4 carbon atoms, and includes methyl, ethyl, isopropyl, 2-methylpropyl etc.

The expression "at corresponding positions with each other" refers to paired positions which are located at a single pair or plurality of pairs of carbon atoms, one member of said pair being on one glucopyranose ring (of trehalose) and the other member being on the other glucopyranose ring, and both members being represented by the same numeral but distinguishable by attaching a prime to one of the two numerals, according to the accepted or recommended nomenclature.

When the compound of the above formula (I) has two or more $C_{1-40}$ aliphatic acyl groups, said groups may be same or different.

One group of compounds according to the present invention are trehalose derivatives of the formula:

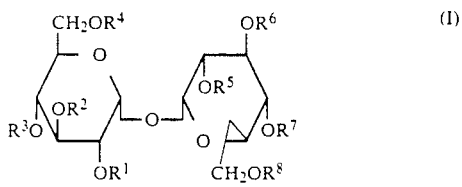

wherein one of $R^1$, $R^2$, $R^3$, $R^4$, $R^5$, $R^6$, $R^7$ and $R^8$ is independently selected from the group consisting of $C_{1-40}$ aliphatic acyl groups and all the rest of them are hydrogen atoms, with the proviso that said one is not 2-palmitoyl or 6-aliphatic acyl.

Within this group of compounds, referred compounds have $C_{1-40}$ aliphatic acyl group at the 2- or 3-position.

Another group of compounds according to the present invention is trehalose derivatives of the formula:

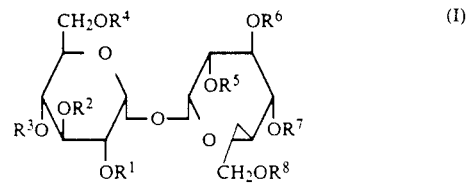

wherein two of $R^1$, $R^2$, $R^3$, $R^4$, $R^5$, $R^6$, $R^7$ and $R^8$ are independently selected from the group consisting of $C_{1-40}$ aliphatic acyl groups and all the rest of them are hydrogen atoms, with the proviso that said two are not located at corresponding positions with each other.

Within this group of compounds, preferred compounds have $C_{1-40}$ aliphatic acyl groups at 2,3- or 2,6'-positions.

A further group of compounds according to the present invention is trehalose derivatives of the formula:

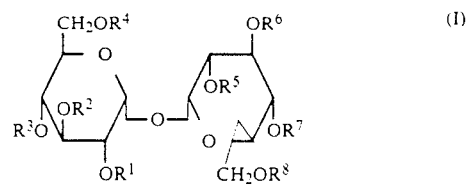

wherein three of $R^1$, $R^2$, $R^3$, $R^4$, $R^5$, $R^6$, $R^7$ and $R^8$ are independently selected from the group consisting of $C_{1-40}$ aliphatic acyl groups and all the rest of them are hydrogen atoms, with the proviso that said three are not 2,3,2'-tripalmitoyl.

Within this group of compounds, preferred compounds have $C_{1-40}$ aliphatic acyl groups at 2,3,6'- or 2,6,6'-positions.

A still further group of compounds according to the present invention is trehalose derivatives of the formula:

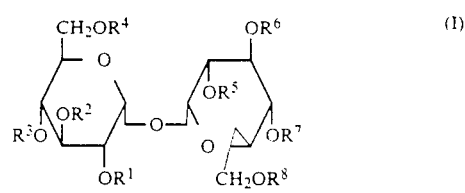

wherein four of $R^1$, $R^2$, $R^3$, $R^4$, $R^5$, $R^6$, $R^7$ and $R^8$ are independently selected from the group consisting of $C_{1-40}$ aliphatic acyl groups and all the rest of them are hydrogen atoms, with the proviso that said four are not located at corresponding positions with each other or 2,3,4,2'- or 2,3,6,2'-positions.

Within this group of compounds, preferred compounds have $C_{1-40}$ aliphatic acyl groups at 2,3,6,6'-positions.

The above compounds of the formula (I) can be prepared by the following process.
(a) Preparation of monoacyl derivatives
(Process i)
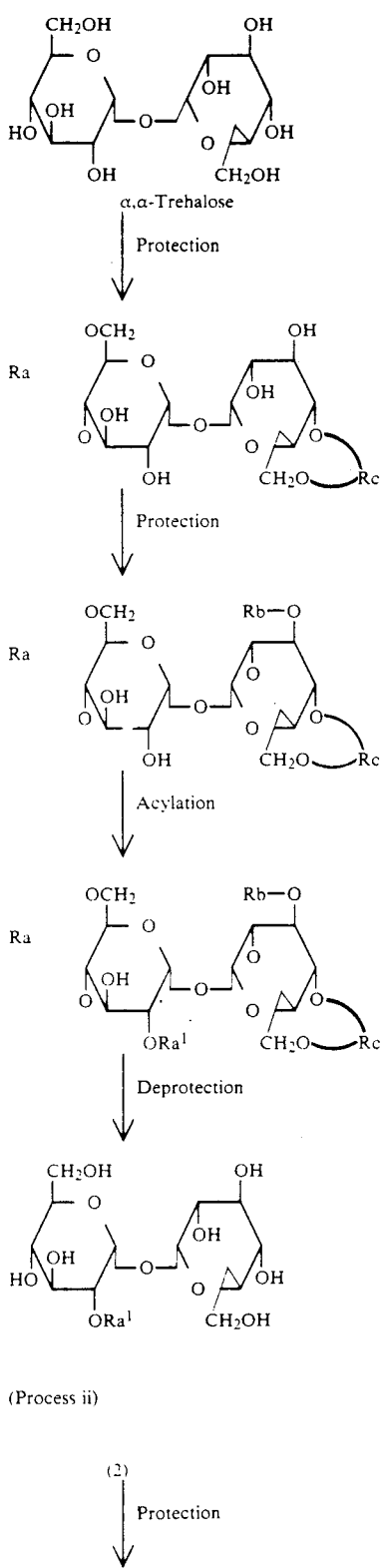
(Process ii)
(2) ↓ Protection
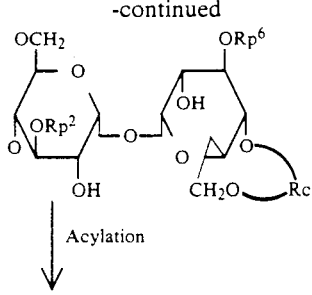
(5)
↓ Acylation
(6)
↓ Deprotection
(Ia)
(Process iii)
(3) ↓ Acylation
(7)
↓ Deprotection
(Ib)
(b) Preparation of diacyl derivatives
(Process iv)
(1) ↓ Protection
(2) ↓ Isomerization Protection
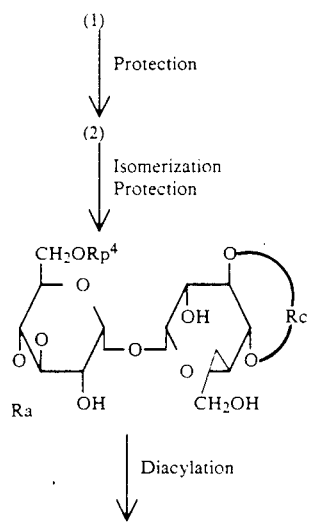
↓ Diacylation -continued (9)

[structure with CH₂ORp⁴, Ra, ORa¹, CH₂ORa⁸, Rc]

↓ Deprotection (10)

[structure with CH₂ORp⁴, HO, OH, ORa¹, CH₂ORa⁸]

↓ Deprotection (Ic)

[structure with CH₂OH, HO, OH, ORa¹, CH₂ORa⁸]

(Process v)

(3)
↓ Diacylation (11)

[structure with OCH₂, Ra, ORa², ORa¹, Rb—O, Rc, CH₂O]

↓ Deprotection (Id)

[structure with CH₂OH, HO, ORa², ORa¹, OH, CH₂OH]

(Process vi)

(4)
↓ Acylation (11)

↓ Deprotection (Id)

(Process vii)

-continued (7)
↓ Acylation (11)

↓ Deprotection (Id)

(c) Preparation of triacyl derivatives
(Process viii)

(3)
↓ Diacylation (11)

↓ Deprotection (12)

[structure with CH₂OH, HO, ORa², ORa¹, Rb—O, OH, CH₂OH]

↓ Protection (13)

[structure with CH₂ORp⁴, HO, ORa², ORa¹, Rb—O, OH, CH₂OH]

↓ Acylation (14)

[structure with CH₂ORp⁴, HO, ORa², ORa¹, Rb—O, OH, CH₂ORa⁸]

↓ Deprotection (Ie)

[structure with CH₂OH, HO, ORa², ORa¹, OH, CH₂ORa⁸]

(Process ix)

(3)
↓ Acylation

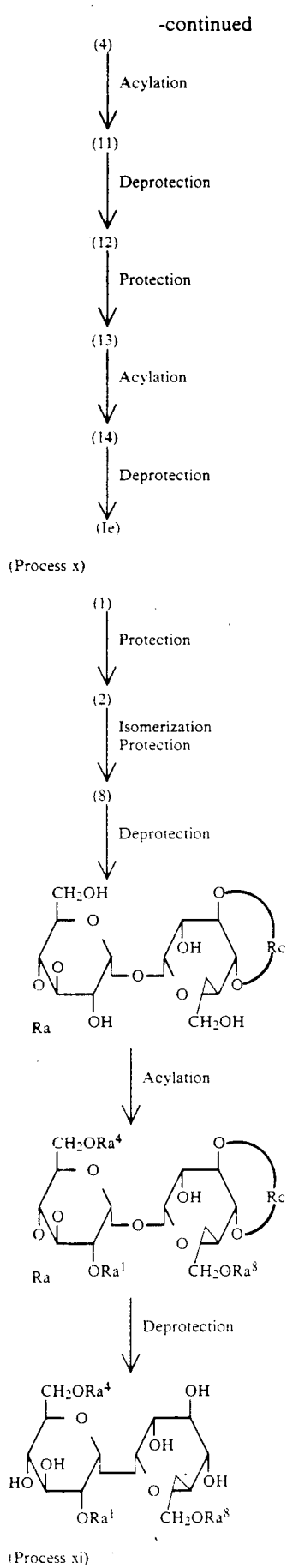

(Process x)

(Process xi)

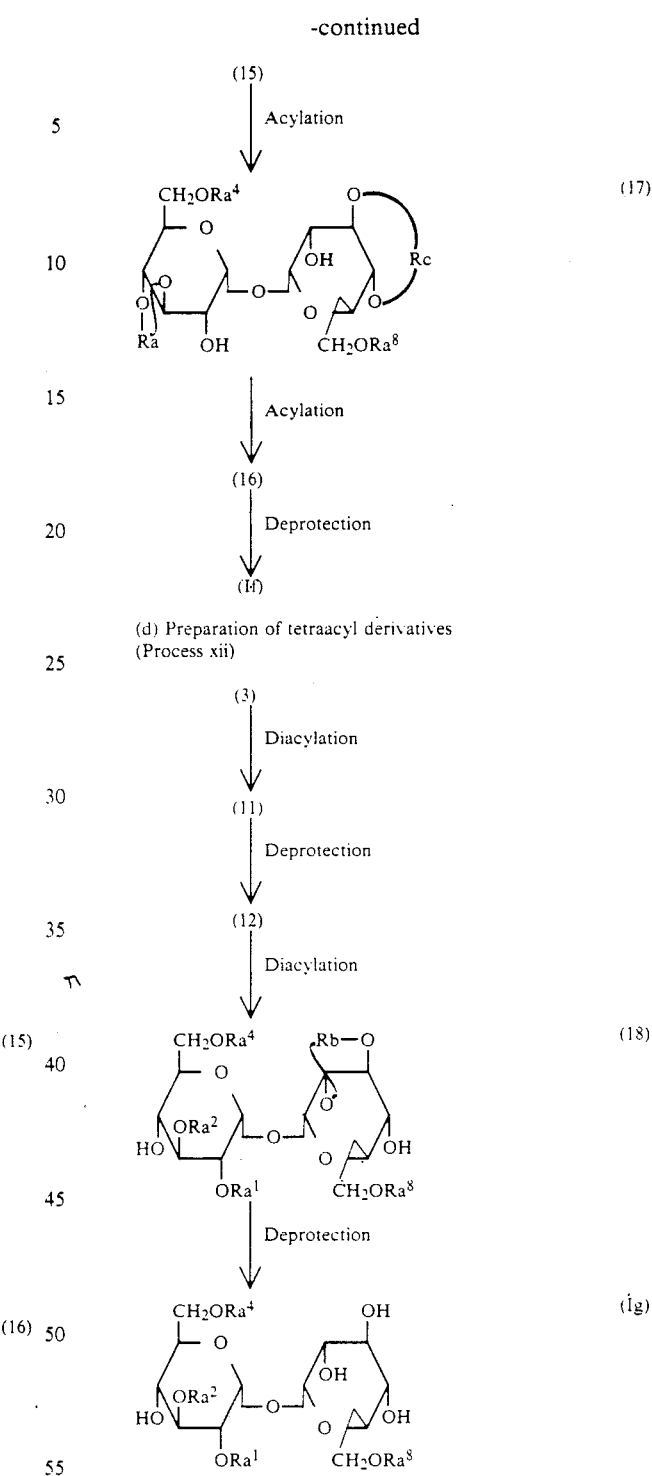

(d) Preparation of tetraacyl derivatives
(Process xii)

In the above formulae, Ra, Rb and Rc are independently bivalent hydroxy-protecting groups. $R^2_p$, $R^4_p$ and $R^6_p$ are independently monovalent hydroxy-protecting groups, and $R^1a$, $R^2a$, $R^4a$ and $R^8a$ are independently $C_{1-40}$ aliphatic acyl groups.

Process i

The reaction for obtaining compound 2 starting from compound 1 ($\alpha,\alpha$-trehalose) is carried out by treating compound 1 with a bivalent hydroxy-protecting group introducing agent (hereinafter, referred to as BHPGIA) which does not transfer other protecting groups of compound 1, preferably aldehydes such as benzaldehyde or ketones, in the presence of a catalyst such as zinc chloride, according to the known method, for example, the method described in J. Org. Chem., 34, 1035 (1969). Compound 3 can be obtained by treating compound 2 with a BHPGIA (preferably one different from the BHPGIA used in the preceding step), for example a silylating agent X-Rb-X wherein Rb is e.g. -Si(i-Pr)$_2$-O- Si(i-Pr)$_2$- and X is halogen, preferably chlorine, in an inert solvent and preferably in the presence of a base such as pyridine or picoline.

The acylation of compound 3 can be effected by reacting an acylating agent capable of introducing a $C_{1-40}$ aliphatic acyl group in an inert solvent e.g. methylene chloride, preferably in the presence of a base such as 4-dimethylaminopyridine.

Said acylating agent may be a carboxylic acid having the desired acyl group or a reactive derivative of said carboxylic acid. Said reactive derivative may be an anhydride with an inorganic or organic acid, an activated ester or an activated amide, for example, acid azide, (esterified)carbonic acid anhydride, (esterified)phosphoric acid anhydride, nitrophenyl ester, pyridylthio ester, ester with N-hydroxysuccinimide, ester with N-hydroxyphthalimide, amide with imidazol etc. When a carboxylic acid is used as the acylating agent, it is advantageous to carry out the reaction in the presence of a condensing agent such as N,N'-dicyclohexylcarbodiimide, N-cyclohexyl-N'-morpholinoethylcarbodiimide, N,N'-diisopropylcarbodiimide, N-ethylbenzisoxazolium salt, 2-chloro-1-methylpyridinium salt, N,N'-carbonyldiimidazol etc. The reaction proceeds at a temperature between cooling and warming, for example at room temperature.

Compound 4 is then subjected to the elimination reaction of the protecting group to give the desired compound Ia. This reaction can be effected by applying the appropriate number of times of removing reaction according to the number of protecting groups or only once when the removing reaction can be applied to all the protecting groups present, said removing reaction being a conventional one for respective protecting groups. For example, the group Rb is removed by using a desilylating agent such as tetrabutylammonium fluoride in an inert solvent at moderate conditions such as at room temperature (see Carbohydr. Res., 138, 55, 1985) and then Ra and Rc such as benzylidene are removed by heating (e.g. at 90° C.) with 90% acetic acid.

This course is preferred for the case where R$^1$a has not any protected substituent or has any unsaturation.

When the compound Ia has unsaturation in R$^1$a, it can be converted to the compound Iae having epoxy substituent in R$^1$a by treating compound Ia with an epoxidizing agent including an organic peracid such as peracetic acid, perbenzoic acid, metachloroperbenzoic acid etc. or hydrogen peroxide or peroxoacid.

Process ii

The reaction for obtaining the compound 5 from compound 2 is carried out by treating compound 2 with a monovalent hydroxy-protecting group introducing agent (hereinafter, referred to as MHPGIA), for example benzylating agent, in an inert solvent, e.g. hexamethyl phosphorictriamide (HMPA), preferably under inert atmosphere (e.g. nitrogen) and in the presence of a stannylating agent, e.g. di-n-butyltin oxide (see, Chem. Pharm. Bull., 33, 2243,1985). When benzyl chloride or benzyl bromide is used as the benzylating agent, the reaction is usually carried out at a temperature between 100° C. and 150° C. A by-product, 2,3'-dibenzyl compound, can be separated by silicagel column chromatography.

The acylation of compound 5 can be carried out in a manner similar to the acylation of compound 3 in Process i.

Removal of the protecting group in compound 6 can be effected by methods conventional and appropriate for particular protecting groups, for example by hydrogen with a metal catalyst for catalytic hydrogenation, e.g. palladium black. In this manner, compound Ia can be produced.

This process is appropriate in the case when R$^1$a to be introduced has one or more protected groups.

Process iii

When a corynomycolic acid residue having a protecting group such as benzyl is to be introduced, the acylation of compound 3 is carried out by a method similar to the acylation in Process i. When another aliphatic acid residue is to be introduced, it can be carried out, using preferably an acid halide as the acylating agent, in an inert solvent (e.g. methylene chloride) and in the presence of a hydrohalide capturing agent, preferably a tertiary amine (e.g. triethylamine, N,N-dimethylaniline etc.), at a relatively lower temperature (e.g. with ice-cooling or at room temperature). In this case, 2-O-acyl derivative of compound 4 may be produced as a by-product but this can be separated in the conventional manner or after carrying out later steps.

Removal of the protecting group in compound 7 can be effected by methods used in Process i or ii. In this way, compound Ib can be obtained.

Process iv

The reaction for obtaining compound 2 from the compound 1 can be carried out by dissolving compound 1 in an inert solvent, preferably in the presence of a base such as pyridine, picoline etc., and treating it with an isomerizing silylating agent X-Ra(or Rc)-X. Liquid bases can serve as a solvent. In the silylating agent, X is preferably chlorine and Ra(or Rc) is preferably -SiR$_2$-O-SiR$_2$- wherein R is isopropyl. The reaction is carried out at lower, elevated or usually room temperature.

The reaction for obtaining compound 8 from compound 2 can be carried out by isomerizing compound 2 produced in the preceding step with an organic base or a salt thereof, for example pyridine hydrochloride, in an inert solvent, e.g. N,N-dimethylformamide. The reaction proceeds at room temperature. An isomeric mixture is obtained in a reaction which can be separated by the conventional way or after the following step.

The product in the above step is then treated with a protecting group introducing agent such as R$^4$p-X wherein X is halogen, for example trityl chloride, in an inert solvent, preferably in the presence of a base which also serve as a solvent, such as pyridine. The reaction proceeds at room temperature and may be accelerated by heating. Separation of the isomeric mixture can be accomplished by the conventional method, for example chromatography (e.g. on silicagel).

The diacylation of compound 8 can be carried out in a manner similar to that for the acylation of the compound 3 or 5. When groups R$^1$a and R$^8$a to be introduced are the same acyl group, these groups may be introduced simultaneously or stepwise into compound 8 produced in the preceding step. When the groups are different, it is desirable to introduce first $R^8a$ and then $R^1a$. The acyl groups to be introduced preferably do not have an epoxy group as substituent and when these have any hydroxy or carboxy substituent, they are preferably protected with protective groups conventional in the saccharide or peptide synthesis.

Acylation can be effected by reacting an acylating agent in an inert solvent e.g. methylene chloride, preferably in the presence of a base such as 4-dimethylaminopyridine.

Said acylating agent may be a carboxylic acid having the desired acyl group or a reactive derivative of said carboxylic acid. Said reactive derivative may be an anhydride with an inorganic or organic acid, an activated ester or an activated amide, for example, acid azide, acid halide, (esterified)carbonic acid anhydride, (esterified)phosphoric acid anhydride, nitrophenyl ester, pyridylthio ester, ester with N-hydroxysuccinimide, ester with N-hydroxyphthalimide, amide with imidazol etc. When a carboxylic acid is used as the acylating agent, it is advantageous to carry out the reaction in the presence of a condensing agent such as N,N'-dicyclohexylcarbodiimide, N-cyclohexyl-N'-morpholinoethylcarbodiimide, N,N'-diisopropylcarbodiimide, N-ethylbenzisoxazolium salt, 2-chloro-1-methylpyridinium salt, N,N'-carbonyldiimidazol etc. The reaction proceeds at a temperature between cooling and warming, for example at room temperature.

Partial deprotection of compound 9 can be carried out by treating the compound produced in the preceding step with a desilylating agent, for example tetrabutylammonium fluoride in an inert solvent. The reaction proceeds under moderate conditions, such as at room temperature.

Deprotection of compound 10 can be carried out by a method conventional for respective protecting groups, for example hydrogenation over a metal catalyst for catalytic hydrogenation, e.g. palladium black for benzyl group, or treatment with an acid catalyst such as HBr or p-toluene sulfonic acid. When $R^1a$ and/or $R^8a$ are saturated, the catalytic hydrogenation is preferred, while when it is unsaturated, acid degradation is desirable. In addition, if $R^1a$ and/or $R^8a$ have any protected substituent, they are preferably removed simultaneously with $R^4p$.

When compound Ic has any unsaturation in $R^1a$ or $R^8a$, it can be converted to compound Ice having an epoxy substituent by treating it with an epoxidizing agent (peroxide) including an organic peracid such as peracetic acid, perbenzoic acid, metachloroperbenzoic acid etc. or hydrogen peroxide or peroxoacid.

Processes v, vi and vii

Diacylation of compound 3 can be carried out in a manner similar to that for the diacylation of compound 8 in Process iv. Thus, when the two acyl groups are introduced in a stepwise fashion, compound 11 is produced via compound 4 or 7, while if they are to be introduced concurrently, compound 11 may be directly produced. When an acyl group has a protected (e.g. with benzyl) hydroxy as the acyl group for $R^2a$, then it is desirable to introduce first $R^2a$ to form compound 7, to which in turn $R^1a$ is introduced.

Deprotection of the compound 11 can be carried out in the same manner as in Processes i, ii, iii or iv giving compound Id.

The compound Id can be converted to the epoxy compound Ide just like compound Ia or Ic. Process viii and ix Compound 11 obtained by Processes v, vi or vii can be partially deprotected to give compound 12. The deprotection can be carried out by a method appropriate for the protective group to be removed, for example by heating (e.g. at 90° C.) with 90% acetic acid in the case of benzylidene.

The produced compound 12 is treated with MHPGIA $R^4p$-X wherein X is halogen, for example trityl chloride, in an inert solvent and preferably in the presence of a base (which can serve as a solvent) such as pyridine at a moderate temperature (e.g. room temperature) to give compound 13. By-products such as 6,6'-protected compound can be removed by silicagel column chromatography.

Acylation of compound 13 can be carried out in a manner similar to that for compound 3,5, or 8.

The produced compound 14 can be deprotected in a manner similar to that for compound 4, 6, 9, 10 or 11 to give compound Ie. If any protected (e.g. with benzyl) hydroxy group is present in the acyl group, such protective group may be concurrently removed by treating with hydrogen in the presence of a metal catalyst for catalytic hydrogenation such as palladium black, if desired.

Processes x and xi

The production of compound 8 from compound 1 ($\alpha,\alpha$-trehalose) via compound 2 can be accomplished in a manner similar to Process iv. For the silylation, see Tetrahedron, 41, 4557, 1985.

Compound 8 can be partially deprotected to give compound 15. This reaction is carried out in an appropriate method for the protective group to be removed, for example, when trityl group is to be removed, using acid catalyst such as p-toluenesulfonic acid at a moderate temperature, e.g. room temperature (see Fukugotoshitsu Kenkyuho (Methods for Research of Complex Carbohydrate) II, Biochemical Society of Japan, page 243, 1986).

Acylation of compound 15 can be carried out in a manner similar to that for compounds 3, 5 and 8. Thus, the three acyl groups $R^1a$, $R^4a$, $R^8a$ and can be introduced concurrently or stepwise via compound 17.

The compound If is obtained by deprotecting the protective groups in compound 16. The deprotecting reaction can be carried out in a manner similar to that for compounds 4, 6, 9, 11 and 14.

Process xii

Production of compound 12 from compound 3 (by diacylation and deprotection) can be carried out simlar to Process viii. Diacylation of compound 12 also can be effected in a manner similar to that for compound 3 or 8 to give the compound 18. Deprotection of the compound 18 is carried out by treating with a desilylation agent, for example tetrabutylammonium fluoride, to give compound Ig. If, however, compound 18 has any protected (e.g. with benzyl) hydroxy group in its acyl group, compound Ig is obtainable after hydrogenating over a metal catalyst for catalytic hydrogenation such as palladium black.

Among the intermediates in the above described processes, the following compounds are novel and thus the present invention provides such compounds as the novel and key intermediates;

Compound of formula (3)

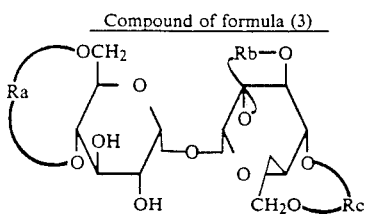

(3)

wherein Ra, Rb and Rc are independently bivalent hydroxy-protecting groups;

Compound of formula (8)

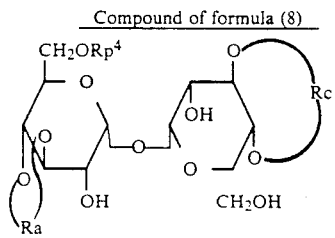

(8)

wherein Ra and Rc are independently bivalent hydroxy-protecting groups and $R^4p$ is hydrogen atom or a monovalent hydroxy-protecting group.

Furthermore, some carboxylic acids usable as the acylating agent in the above described processes are novel. Examples of such carboxylic acids are α-alkyl-β-hydroxy acid (having basic structure of mycolic acid) of the formula:

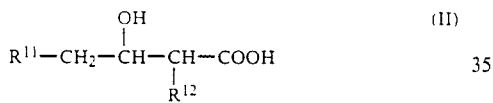

(II)

wherein $R^{11}$ and $R^{12}$ are independently alkyl, which can be produced, for example, by the following processes.

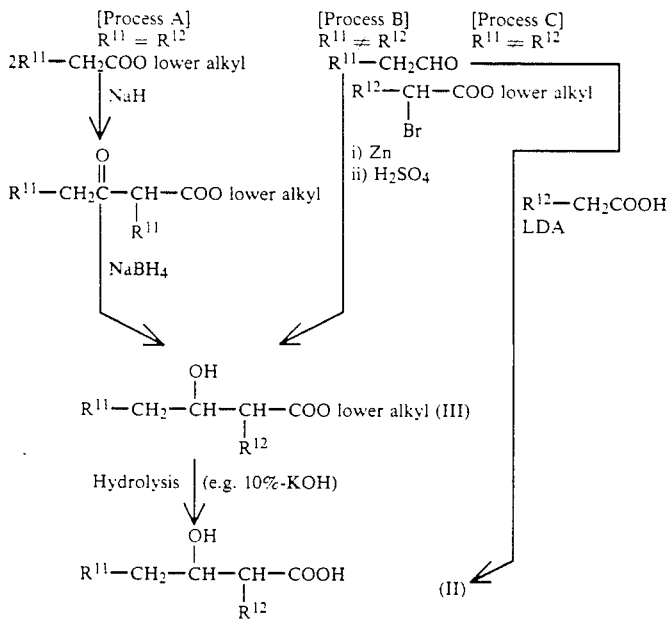

According to Process A, for the preparation of branched aliphatic acid like α-alkyl-β-hydroxy aliphatic acid II, when $R^{11}$ and $R^{12}$ are the same alkyl, an aliphatic acid ester can be subjected to Claisen condensation and then reduced with NaBH$_4$ to give the desired ester III, according to the description in the literature (Bull. Soc. Chim. Fr., 504–510, 1954).

According to Process B, when $R^{11}$ and $R^{12}$ are different with each other, an aliphatic aldehyde and an α-bromocarboxylic ester can be condensed by Reformatsky reaction to give Compound III. Compound III produced by Process A or B is hydrolyzed to give the desired compound, α-alkyl-β-hydroxy acid II.

In addition, according to Process C, when $R^{11}$ and $R^{12}$ are different alkyl, an aliphatic aldehyde and a carboxylic acid can be condensed in the presence of, preferably two moles or more of, a strong base such as LDA (lithium diisopropylamide) to directly give the compound II.

In the above processes, when a hydroxy acid such as above is to be used in the acylation as the third step, it is necessary to protect the hydroxy function. A preferred example of such protecting process is shown below.

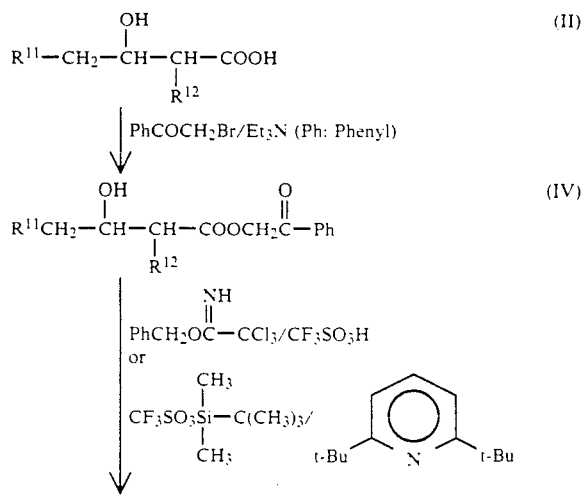

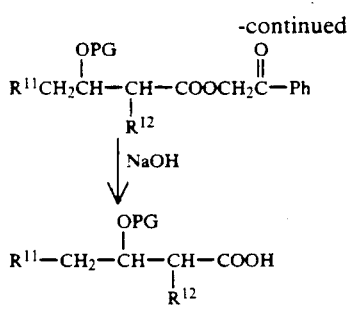

Compound II is treated with phenacyl bromide to give the phenacyl ester IV.

The ester IV in turn is treated with benzyl trichloroacetimidate in the presence of an acid to form compound V having benzyl type protection or with t-butyldimethylsilyltrifluoromethanesulfonate in the presence of a base to form compound V having silyl type protection. The phenacyl moiety in the produced compound V can be removed to give the desired aliphatic acid VI.

The compounds I of the present invention have a pronounced anti-tumor activity and therefore are useful in the preparation of a medicament.

The compounds of the invention are effective in the treatment of various kind of tumors, as indicated in proliferation tests with various tumor cells. For example, in vivo antitumor activity can be tested using Erlich carcinoma, which is subcultured in ascites of DS male mice and then transplanted in dorsal skin of healthy mice at $3 \times 10^6$ cells per animal. Test compounds are administered daily for several days to 30 days and tumor weights are compared with controls. In this test, the compounds of the invention are proved to be effective for inhibiting proliferation of tumor cells. Thus, the compounds of the invention can be used in the treatment of, for example, cancers of the breast, the prostate, the colon, the pancreas and the brain.

For the above indication, the appropriate dosage will, of course, vary depending upon the particular compound employed, the host, the mode of administration, and the condition being treated. However, in general, satisfactory results can be obtained at daily dosage from about 0.1 to 50 mg/kg body weight. For larger animals such as human, the daily dosage is in the range of approximately 10 mg to 2 g.

The following non-limiting Examples further illustrate the present invention.

In the Examples, silicagel for column chromatography is Merck #7734 and sheet for TLC is Merck plastic sheet #5735.

The invention will be now further illustrated by means of the following examples, which are not, however, intended to limit the scope of the invention.

Preparation of the starting material

REFERENCE EXAMPLE 1

Preparation of 3-hydroxy-2-n-tetradecyl-docosanoic acid (II) (Process B)

Zinc (352.7 mg, 5.40 millimole) was suspended in a mixed solvent (9 ml) of dry benzene and dry tetrahydrofuran (5:1) under argon atmosphere. Trimethylchlorosilane (0.05 ml, 0.40 millimole) was added dropwise to the suspension, and the mixture was stirred at room temperature for 15 minutes, then refluxed (at bath temperature of 85° C.) and cooled to the room temperature.

Icosanal (1 g, 3.37 millimole) and methyl 2-bromohexadecanoate (977.8 mg, 2.80 millimole) were dissolved in the same mixed solvent (30 ml). The obtained solution (4 ml) was added dropwise to the reaction vessel containing zinc activated by trimethylchlorosilane as described above, and the mixture was stirred at 85° C. for 1 hour. The progress of reaction was confirmed through thin layer chromatography, and the rest of the solution (26 ml) was gradually added under the same conditions and the mixture was stirred for 8 hours. After cooling the reaction mixture with ice, 20% sulfuric acid (50 ml) was added thereto, and the, mixture,, was stirred for 15 minutes. Then the mixture was extracted twice with benzene, and the organic phase was washed twice with 10% sulfuric acid, and successively washed once with saturated aqueous sodium bicarbonate solution, once with 10% sulfuric acid, then twice with water, and dried over anhydrous sodium sulfate. The solvent was distilled off from the organic phase, and the obtained residue was dissolved in a developing solvent (n-hexane:ether=8:2) and fractionated through silicagel column chromatography (n-hexane:ether=8:2). The fourth and fifth fractions were pooled and the solvent was distilled off to give methyl 3-hydroxy-2-n-tetradecyl-docosanoate (III) (812.8 mg, yield 51%) in the form of white crystals.

The white crystals (5.16 g, 9.1 millimole) was dissolved in a mixed solvent (144 ml) of dioxane and ethanol (1:5), with heating and 10% potassium hydroxide solution (51 ml, 91 millimole) was added thereto and the mixture was refluxed for 1 hour. The reaction mixture was acidified (pH:about 2) with 2N hydrochloric acid with cooling on ice, and the precipitates were filtered off, washed and dried. The obtained product was fractionated through silicagel column chromatography (chloroform:methanol=95:5). The first two fractions comprising impurities were discarded and the colorless third fraction was pooled, and the solvent, was distilled off from the fraction to give 3-hydroxy-2-n-,tetradecyl-docosanoic acid (II) (1.469 g, yield 29%) in the form of white solid, m.p. 65°-67° C.

REFERENCE EXAMPLE 2

Preparation of 3-benzyloxy-2-n-tetradecyl-octadecanoic acid (VI) (protection of hydroxyl group of (II))

3-Hydroxy-2-n-tetradecyl-octadecanoic acid (II) prepared as described [Bulletin de la Societe chimique de France 504–510 (1954)] was dissolved in dry tetrahydrofuran (45 ml), and then phenacyl bromide (2.70 g, 13.59 millimole) and triethyl amine (1.89 ml, 13.59 millimole) were successively added thereto with ice cooling. The mixture was allowed to warm to the room temperature, and reacted for 23 hours. The insoluble mass in the reaction mixture was filtered off with suction and the solvent was distilled from the filtrate. The residue was dissolved in benzene and the obtained solution was fractionated through silicagel column chromatography (benzene). After the fractions comprising impurities were discarded, the later colorless fractions were pooled, and the solvent was distilled off from the fraction to, give white crystals of phenacyl 3-hydroxy-2-n-tetradecyl-octadecanoate (IV) (1.81 g, yield 33%).

Then, phenacyl 3-hydroxy-2-n-octadecyl-octadecanoate (IV) (1.81 g, 2.94 millimole) was dissolved in dry methylene chloride (80 ml) under, argon atmosphere, and benzyl 2,2,2-trichloro-acetimidate (0.66 ml, 3.53 millimole) and trifluoromethane sulfonic acid (0.052 ml, 0.59 millimole) were successively added dropwise thereto with ice cooling. The reaction mixture was allowed to warm to room temperature, and to react for 17 hours, then methylene chloride was added to the reaction mixture, and the obtained solution was successively washed with saturated aqueous sodium bicarbonate solution and water, and then dried over anhydrous sodium sulfate. The solvent was distilled off from the solution. The residue was dissolved in a developing solvent (benzene:n-hexane=6:4), and fractionated through silicagel column (benzene:n-hexane=6:4), and the fast eluting fractions comprising impurities were discarded and then the later colorless fractions were pooled and the solvent was distilled off to give phenacyl 3-benzyloxy-2-n-tetradecyl-octadecanoate (V) (783.9 mg) in the form of colorless oil.

Further, the same procedure was repeated using the recovered starting material (IV), and compound (V) (1.0264 g) was obtained in a total yield of 1.8103 g (yield 87%).

Finally, phenacyl 3-benzyloxy-2-n-tetradecyl-octadecanoate (V) (1.81 g, 2.57 millimole) was dissolved in a mixed solvent (70 ml) of tetrahydrofuran and methanol (1:1) and 1N sodium hydroxide (7.70 ml, 7.70 millimole) was added thereto, and the mixture was reacted at 65° C. for 2.5 hours. The solvent was distilled off from the reaction mixture, and water and tetrahydrofuran were added to dissolve the residue. Then the solution was acidified with 2N hydrochloric acid (to pH of about 2) with ice cooling, and extracted with ethyl acetate, and the organic phase was washed with water and dried over anhydrous sodium sulfate. The solvent was distilled off from the organic phase, the residue was dissolved in a developing solvent (n-hexane:ethyl acetate=8:2), and the obtained solution was purified over a silicagel column (n-hexane:ethyl acetate=8:2). The fast eluting fractions comprising impurities were discarded and the later colorless fractions were pooled. The solvent was evaporated off from the pooled fractions, and the residue was purified over a silicagel column (benzene:ethyl acetate=9:1) again, to give 3-benzyloxy-2-n-tetradecyl-octadecanoic acid (VI) (878 mg, yield 58%) in the form of colorless oil.

REFERENCE EXAMPLE 3

Preparation of 3-benzyloxy -2n-tetradecyl-docosanoic acid(VI)

(protection of hydroxyl group of (II))

3-Hydroxy-2-n-tetradecyl-docosanoic acid (II), prepared by the Reformatsky reaction (process B) and hydrolysis as described in Reference example 1, was subjected to phenacylesterification, acidic benzylation followed by deprotection by hydrolysis, to give 3-benzyloxy-2-n-tetradecyl-docosanoic acid (VI) in the form of pale yellow oil.

REFERENCE EXAMPLE 4

Preparation of 3-hydroxy-2-n-tetradecyl-11-icosenoic acid (II) (process C)

Diisopropyl amine (5.04 ml, 36.02 millimole) and dry tetrahydrofuran (30 ml) were introduced into a reaction vessel sufficiently substituted by argon gas. The reaction mixture was cooled to −78° C., and then 1.6M butyl lithium/hexane solution (23.64 ml, 37.82 milli-mole) was added dropwise thereto. The cooling bath was removed and the solution was allowed to warm to 0° C. and stirred for 30 minutes at the same temperature. The lithium diisopropylamide/tetrahydrofuran solution was again cooled to −78° C., and palmitic acid (4.62 g, 18.02 millimole) in dry tetrahydrofuran (60 ml) was added thereto, and the reaction mixture was stirred for 15 minutes at the same temperature (−78° C.). Then, the reaction temperature was raised to room temperature, and the reaction was continued for 1 hour. The reaction mixture was again cooled to −78° C., and 9-octadecenal (4 g, 15.02 millimole) in dry tetrahydrofuran (60 ml) was added dropwise thereto. The obtained mixture was reacted for 4 hours under the same conditions, and allowed to warm to 0° C., and the reaction was stopped by adding 1N hydrochloric acid (200 ml). The reaction mixture was extracted thrice with chloroform. The organic phase was washed twice with water and then dried over anhydrous sodium sulfate. The inorganic salt was filtered off and the solvent was distilled off from the filtrate. The obtained residue was dissolved in a developing solvent and fractionated through silicagel chromatography (n-hexane:ethyl acetate=8:2→chloroform:methanol=95:5) to give 3-hydroxy-2-n-tetradecyl-11-icosenoic acid (II)(3.73 g, yield 47.5%) in the form of white viscous solid.

REFERENCE EXAMPLE 5

Preparation of phenacyl 3-hydroxy-2-n-tetradecyl-11-icosenoate (IV)(Esterfication of carboxylic acid)

3-Hydroxy-2-n-tetradecyl-11-icosenoic acid (II)(3.68 g, 7.04 millimole) was dissolved in dry tetrahydrofuran (100 ml), and phenacyl bromide (2.10 g, 10.56 millimole) and triethyl amine (1.47 ml, 10.56 millimole) were successively added thereto with ice cooling. The reaction mixture was allowed to warm to room temperature, and to react for 13.5 hours. The insoluble matter in the reaction mixture was filtered off with suction and the solvent was distilled off from the filtrate. The residue was dissolved in methylene chloride and the obtained solution was successively washed with water and saturated aqueous sodium chloride solution, and dried over anhydrous sodium sulfate. The inorganic salt was filtered off and the solvent was distilled off from the filtrate. The obtained residue was purified over a silicagel column (benzene ⟶ benzene:ethyl acetate=8:2) to give phenacyl 3-hydroxy-2-n-tetradecyl-11-icosenoate (IV)(998.6 mg, yield 22.1%) in the form of white viscous solid. IR($\nu_{max}$KBr, cm$^{-1}$): 3340, 2900, 2850, 1740, 1705

Reference Example 6

Preparation of 3-(t-butyldimethylsilyloxy)-2-n-tetradecyl-11-icosenoic acid (VI)(Preparation of hydroxyl-protected product)

Phenacyl 3-hydroxy-2-n-tetradecyl-11-icosenoate (IV)(820 mg, 1.28 millimole) was dissolved in dry methylene chloride (8 ml), and 2,6-di-t-butylpyridine (0.72 ml, 3.2 millimole) was added. Then, t-butyl-dimethylsilyltrifluoromethane sulfonate (0.44 ml, 1.92 millimole) was added dropwise thereto. The reaction mixture was allowed to react at room temperature for 30 minutes, and water (80 ml) was added thereto and the obtained solution was extracted twice with methylene chloride. The organic phase was dried over anhydrous sodium sulfate, and the inorganic salt was filtered off, and the solvent was distilled off from the filtrate. The obtained residue was purified over a silicagel column (n-hexane:ether=98:2) to give phenacyl 3-(t-butyldimethylsilyloxy)2-n-tetradecyl-11-icosenoate(V) (798 mg, yield 82.6%) in the form of colorless oil.

IR ($\nu_{max}$KBr,cm$^{-1}$); 2900, 1750, 1710

$^1$H-NMR(CDCl$_3$, δ); 0.04(s, 6H, —CH$_3$×2), 0.86(s,9H, —C(CH$_3$)$_3$), 0.58-3.00(m, 61H, —CH$_2$, —CH$_3$), 4.89(m, 1H, —CHOH), 5.15-5.46(m, 4H, —CH=CH—, Ph—CH$_2$—), 7.31-7.96(m, 5H, Ar—H)

Phenacyl 3t-(t-butyldimethyl siloxy)-2-n-tetradecyl-11icosenoate (V)(798 mg, 1.06 millimole) was dissolved in a mixed solvent of tetrahydrofuran (15.8 ml) and methanol (15.8 ml), and 1N sodium hydroxide solution (3.2 ml) was added. The reaction mixture was heated for 1.5 hours at 70° C., and water (150 ml) was added thereto. The reaction mixture was acidified with 2N hydrochloric acid (pH:about 2) and was extracted twice with ethyl acetate. The organic phase was washed with water and dried over anhydrous sodium sulfate, and the inorganic salt was filtered off, and the solvent was distilled off from the filtrate. The obtained residue was purified over a silicagel column (n-hexane:ethyl acetate=93:7) to give 3-(t-butyldimethylsilyloxy)-2- n-tetradecyl-11-icosenoic acid (VI)(410 mg, yield 60.9%) in the form of pale yellow oil.

IR ($\nu_{max}$KBr,cm$^{-1}$); 2910, 1710

$^1$H-NMR(CDCl$_3$, δ); 0.10(s, 6H, —CH$_3$×2), 0.89(s,9H, —C(CH$_3$)$_3$), 0.66-2.70(m, 61H, —CH$_2$, —CH$_3$), 3.68-4.00(m, 1H, —CHOH), 5.18-5.51 (m, 2H, —CH=CH—)

Reference Example 7

Preparation of 3-hydroxy-2-n-tetradecyl-octadecanoic acid (II) (Process C)

Diisopropyl amine (0.70 ml, 4.99 millimole) and dry tetrahydrofuran (3.75 ml) were introduced into a reaction vessel sufficiently substituted by argon gas. The reaction mixture was cooled to −78° C., and then 1.6M butyl lithium/hexane solution (3.28 ml, 5.24 millimole) was added dropwise thereto. The cooling bath was removed and the solution was allowed to warm to 0° C., and stirred for 30 minutes at the same temperature. The lithium diisopropylamide/tetrahydrofuran solution was again cooled to −78° C., and hexadecanoic acid (639.9 mg, 2.50 millimole) in dry tetrahydrofuran (3.75 ml) was added thereto, and the reaction mixture was stirred for 15 minutes at the same temperature (−78° C.). Then, the reaction temperature was raised to room temperature, and the reaction was continued for 1 hour. The reaction mixture was again cooled to −78° C., hexadecanal (500 mg, 2.08 millimole) in tetrahydrofuran (6.25 ml) was added dropwise thereto. The obtained mixture was allowed to react under the same conditions for 2 hours, then allowed to warm to 0° C., and the reaction was stopped by adding 1N, hydrochloric acid (25 ml). The reaction mixture was extracted three times with chloroform. The organic phase was washed twice with water and then dried over anhydrous sodium sulfate. The solvent was distilled off and the residue was purified on silicagel chromatography (n-hexane:ethyl acetate=8:2 → chloroform:methanol=9:1). The fast eluting fractions were discarded, and the later colorless fractions were pooled, and the solvent was distilled off from the pooled solution to give 3-hydroxy-2-n-tetradecyl-octadecanoic acid (II)(475.5 mg yield 46%) in the form of white solid.

Process i

Reference Example i - 1

Preparation of 4,6,4', 6'-di-O-benzylidene-α,-60-trehalose (2)

Anhydrous α,α-trehalose (1)(10 g, 27.7 millimole) and zinc chloride (50 g, 36.7 millimole) were suspended in benzaldehyde (90 ml) as described in the literature, and the suspension was stirred vigorously at room temperature for 20 hours. Water(200 ml) was added to the reaction mixture. The solution was stirred for a while, and petroleum ether (200 ml) was added thereto. Then, the precipitates were filtered off, washed with water, and dissolved in ethylacetate. The solution was dried over anhydrous sodium sulfate. The inorganic salt was filtered off and the solvent was distilled off. The obtained residue was recrystallized from ethyl acetate/n-hexane to give 4,6,4', 6'-di-O-benzylidene-α,α-trehalose (2)(6.09 g, yield 40.2%) in the form of white solid, m.p. 194°-196° C. (after recrystallization) [reference value:195° C. (ethanol)] (literature: Journal of organic chemistry, 34, 1035(1969)).

Reference Example i-2

Preparation of 4,6,4', 6'-di-O-benzylidene-2,3-O(tetraisopropyldisiloxane-1,3-diyl)-α,α-trehalose (3)

To a solution of 4,6,4', 6'-di-O-benzylidene-α,α-trehalose (2) (2.10 g, 4.05 millimole) dissolved in dry pyridine (11 ml) was added 1,3-dichloro-1,1,3,3-tetraisopropyldisiloxane (1.53 ml, 4.84 millimole) dropwise, and the mixture was stirred at room temperature for 24 hours. The solvent was distilled off and the residue was dissolved in chloroform. The solution was washed with saturated sodium bicarbonate solution and saturated sodium chloride solution. The organic phase was dried over anhydrous sodium sulfate, which was removed by filtration, and the solvent was distilled off from the filtrate. The residue was purified over a silicagel column (benzene:ethyl acetate=7:3), and the mixture was again purified by column chromatography to give 4,6,4', 6'-di-O-benzylidene-2,3-O-(tetraisopropyldisiloxane-1,3-diyl)-α,α-trehalose (3) (1.48 g, yield 48.1%) in the form of white foamy solid (m.p. 106°-108° C., after column chromatography)

IR ($\nu_{max}$KBr,cm$^{-1}$); 3420, 2940. 2850

[α]$_D^{20}$; +40.80 (C=1.0, CHCl$_3$). Analysis:Calculated for C$_{38}$H$_{56}$O$_{12}$Si$_2$:C, 59.97;H, 7.42. Found: C, 59.89; H, 7.56.

$^1$H-NMR(CDCl$_3$,δ); 0.87-1.33 (m, 24H, (CH$_3$)$_2$=CH—). 1.53-4.83 (m, 18H, glucoside, (CH$_3$)$_2$=CH—). 5.07-5.27 (m, 2H, Ph—C/e,uns/H/=) 5.53 (d, 2H, anomer H). 7.23-7.60 (m, 10H, Ar-H)

Reference Example i-3

Preparation of 4,6,4', 6'-di-O-benzylidene-2-O-oleoyl-2', 3'-O-(tetraisopropyldisiloxane-1,3-diyl)-α,α-trehalose (4)

To a solution of 4,6,4',6'-di-O-benzylidene-2,3--O-(tetraisopropyldisiloxane-1,3-diyl)-α,α-trehalose (3)(500 mg) 0.657 millimole) dissolved in dry methylene chloride (8 ml) were added oleic acid (0.252 ml, 0.788 millimole), 4-dimethyl aminopyridine (48.2 mg, 0.394 millimole) and N,N'-dicyclohexylcarbodiimide (162.7 mg, 0.788 millimole) successively. The mixture was allowed to react at room temperature for 16 hours, and the solvent was distilled off. The residue was purified by silicagel column chromatography (benzene:ethyl acetate=95:5) to give 4,6,4',6'-di-O-benzylidene-2-O-oleoyl-2',3'-O-(tetraisopropyldisiloxane-1,3-diyl)-α,α-trehalose (4) in the form of colorless viscous product (596.3 mg, yield 88.5%).

Example i-1

Preparation of 2--O-oleoyl-α,α-trehalose (Ia-1)

To a solution of 4,6,4',6'-di-O-benzylidene-2-O-oleoyl-2,',3'-O-(tetraisopropyl-disiloxane-1,3-diyl)-α,α-trehalose (4)(547.5 mg, 0.53 millimole) dissolved in a mixed solvent of dry tetrahydrofuran (17.4 ml), dry acetonitrile (17.4 ml) and water (1.74 ml) was added 1M tetrabutylammonium fluoride in tetrahydrofuran (3.4 ml). The mixture was allowed to react at room temperature for 2 hours, combined with chloroform (200 ml), washed with water and dried over anhydrous sodium sulfate. The inorganic salt was filtered off and the solvent was distilled off from the filtrate. The residue was purified over a silicagel column (benzene:ethyl acetate=1:1) to give desilylated product (450 mg) in the form of white solid.

The desilylated product (418 mg) was dissolved in acetic acid (100 ml), and water (6.0 ml) was added thereto. The mixture was allowed to react at 90° C. for 1 hour, and the solvent was distilled off from the reaction mixture. The residue was purified over a silicagel column (chloroform:methanol=8:2) to give 2-O-oleoyl-α,α-trehalose (Ia-1) (179 mg, yield 55.2%) of white viscous solid, m.p. 90°-100° C.

The compounds (Ia) in the following Table 1, i.e. 2-O-pentadecanoyl-α,α-trehalose (Ia-3), 2-O-(12-hydroxy-stearoyl)- α,αtrehalose (Ia-4) and 2-O-(9,12-octadecadienoyl)-α,α-trehalose (Ia-5), were prepared as described in the above example.

Example i-2

Preparation of 2-O-(9,10-epoxystearoyl)-α,α-trehalose (I ae-1)

A solution of 2-O-oleoyl-α,α-trehalose (Ia) (70 mg, 0.115 millimole) in chloroform (6 ml) was added dropwise to m-chloroperbenzoic acid (45.5 mg, 0.185 millimole) in chloroform (6 ml) with ice cooling, and the mixture was allowed to warm to room temperature and to react for 4 hours. Chloroform (40 ml) was added thereto. The reaction mixture was successively washed with 10% sodium sulfite solution, saturated sodium bicarbonate solution, water and saturated sodium chloride solution, and then dried over anhydrous sodium sulfate. The inorganic salt was filtered off and the solvent was removed from the filtrate. Ethanol was added to the residue and the insoluble mass was filtered off with suction. The solvent was distilled off from the filtrate to give 2-O-(9,10-epoxystearoyl)-α,α-trehalose (Iae-1) (49.8 mg, yield 69.3%) in the form of white foamy solid, m.p. 55°-65° C.

Process ii

Reference Example ii-1

Preparation of 3,3'-di-O-benzyl-4,6,4',6'-di-O-benzylidene-α,α-trehalose (5)

In dry hexamethylphosphoric-triamide (12 ml) was suspended 4,6,4',6'-di-O-benzylidene-α,α-trehalose (2) (400 mg, 0.77 millimole) and dibutyltinoxide (575 mg, 2.31 millimole) and the suspension was allowed to react at 150° C. for 2 hours (the reagent was gradually dissolved). Under the same conditions, benzylbromide (0.366 ml, 3.08 millimole) was added dropwise thereto, and the mixture was allowed to react for additional 2 hours. The reaction mixture was poured onto ice, and extracted with chloroform. The organic phase was washed with saturated sodium chloride solution and dried over anhydrous sodium sulfate. The inorganic salt was filtered off and the solvent was distilled off from the filtrate under reduced pressure (up to 98° C./5 mmHg). The residue was purified over a silicagel column (methylene chloride:esther=9:1) to give 3,3'-di-O-benzyl-4,6,4',6'-di-O-benzylidene-α,αtrehalose (5)(88.7 mg, yield 16.5%).

Reference Example ii-2

Preparation of 2-O-(3-O-benzylcorynomycoloyl-3,3'-di-O-benzyl-4,6,4'6'-di-O-benzylidene-α,αtrehalose (6)

A solution of 3,3'-di-O-benzyl-4,6,4',6'-di-O-benzylidene-α,α-trehalose (5) (82 mg, 0.12 millimole) dissolved in dry methylene chloride (2ml) was combined with 3-O-benzylcorynomycolic acid (170 mg, 0.29 millimole) in dried methylene chloride (3 ml), 4-dimethylaminopyridine (17.3 mg, 0.14 millimole) and N,N'-dicyclohexylcarbodiimide (61 mg, 0.29 millimole) and the mixture was allowed to react at room temperature for 6 hours. The insoluble matter was filtered off and the solvent was distilled off from the reaction mixture. The residue was purified over a silicagel column (n-hexane:ethyl acetate=75:25) to give 2-0-(3-O-benzylcorynomycoloyl)-3,3'-di-O-benzyl-4,6,4',6'-di-O-benzylidene-α,α-trehalose (6) (93.7 mg, yield 61.6 %) in the form of colorless thick product.

Example ii-1

Preparation of 2-O-corynomycoloyl-α,α-trehalose (Ia-2)

To a solution of 2-0-(3-O-benzylcorynomycoloyl)-3,3'-di-O-benzyl-4,6,4',6'-di-O-benzylidene-α,α-trehalose (6) (89.9 mg, 0.071 millimole) dissolved in a mixed solvent of dry methanol (1.2 ml) and dry methylene chloride (1.2 ml) was added palladium black (89.9 mg). The reaction mixture was hydrogenated at room temperature for 15 hours. The palladium black was filtered off from the reaction mixture, and the solvent was distilled off from the filtrate. The obtained residue was purified over a silicagel column (chloroform:methanol=8:2) to give 2-O-corynomycoloyl-α,α-trehalose (Ia-2) (57 mg, yield 97.8%) in the form of white solid, m.p. 95°-105° C.

Process iii

Reference Example iii-1

Preparation of 3-O-(3-O-benzylcorynomycoloyl)-4,6,4',6'-di-O-benzylidene-2'3'-O-(tetraisopropyldisiloxane-1,3-diyl)-α,α-trehalose (7)

Into dry methylene chloride (2.6 ml) was dissolved 4,6,4',6'-di-O-benzylidene-2',3'-O-(tetraisopropyl-disiloxane-1,3-diyl)-α,α-trehalose(3) (81 mg, 0.106 millimole) under argon atomosphere, and 3-O-benzylcorynomycolic acid (150 mg, 0.256 millimole), 4-dimethylaminopyridine (16 mg, 0.128 millimole), and N,N'-dicyclohexylcarbodiimide (53 mg, 0.256 millimole)

were successively added. The mixture was allowed to react at room temperature for 22 hours. The solvent was distilled off from the reaction mixture, and the obtained residue was purified over a silicagel column (n-hexane:ether=75:25) to give 3-O-(3-O-benzyl-corynomycoloyl)-4,6,4',6'-di-O-benzylidene-2',3'-O-(tetraisopropyldisiloxane-1,3diyl)-α,α-trehalose (7) (104 mg, yield 73.8%) in the form of colorless oil.

Reference Example iii-2

Preparation of 4,6,4',6'-di-O-benzylidene-3-O-palmitoyl-2',3'-O-(tetraisopropyldisiloxane-1,3diyl)-α,α-trehalose (7)

Into dry methylene chloride (10 ml) was dissolved 4,6,4',6'-di-O-benzylidene-2', 3'-O-(tetraisopropyl-disiloxane-1,3-diyl)-α,α-trehalose (3) (300 mg, 0.39 millimole) and triethyl amine (0.139 ml, 0.59 millimole) and palmitoyl chloride (167.2 mg, 0.59 millimole) in dry methylene chloride (3 ml) were successively added dropwise thereto with ice cooling. The reaction mixture was allowed to warm to room temperature and to react for 17 hours; then was diluted by adding methylene chloride. The organic phase was successively washed with saturated aqueous sodium bicarbonate solution and water, and dried over anhydrous sodium sulfate. The inorganic salt was filtered off and the solvent was distilled off from the filtrate. The residue was purified over a silicagel column (benzene:ethyl acetate=9:1) to give a mixture of 4,6,4',6'-di-O-benzylidene-3-O-palmitoyl-2', 3'-O-(tetraisopropyldisiloxane-1,3-diyl)-α,α-trehalose (7) and 4,6,4',6'-di-O-benzylidene-2-O-palmitoyl-2', 3'-O-(tetraisopropyldisiloxane-1,3-diyl)-α,α-trehalose (4) (235.0 mg) in the form of colorless viscous product.

Example iii-1

Preparation of 3-O-corynomycoloyl-α,α-trehalose (Ib-1)

Into a mixed solvent of dry tetrahydrofuran (8 ml), dry acetonitrile (4.8 ml) and water (0.48 ml) was dissolved 3-O-(3-O-benzylcorynomycoloyl)-4,6,4',6'-di-O-benzylidene-2', 3'-O-(tetraisopropyldisiloxane-1,3-diyl)-α,α-trehalose (7) (170mg, 0.128 millimole) and 1M tetrabutylammonium fluoride in tetrahydrofuran (1.28 ml) was added thereto. The mixture was allowed to react at room temperature for 1 hour, and combined with chloroform (200 ml), washed with water and dried over anhydrous sodium sulfate. The inorganic salt was filtered off and the solvent was distilled off from the filtrate. The obtained residue was purified over a silicagel column (benzene:ethyl acetate=75:25) to give desilylated product (59.6 mg) in the form of colorless oil.

The desilylated product (59.6 mg) was dissolved in a mixed solvent of dry methylene chloride (4 ml) and dry methanol (4 ml) and the mixture was hydrogenated over palladium black (60 mg) at room temperature for 17 hours. The palladium black was filtered, off from the reaction mixture and the solvent was distilled off from the filtrate. The residue was purified over a silicagel column (chloroform:methanol=85:15) to give 3-O-corynomycoloyl-α,α-trehalose (Ib-1) (39.3 mg, yield 37.4%) in the form of white waxy solid, m.p. 203°-209° C.

The compound (Ib) in the Table 1, i.e. 3-O-(3-hydroxy-2-n-tetradecyl-docosanoyl)-α,α-trehalose (Ib-3) was prepared as described in the above Example.

Example iii-2

Preparation of 3-O-palmitoyl-α,α-trehalose (Ib-2)

A mixture (235.0 mg) of 4,6,4',6'-di-O-benzylidene-3-O-palmitoyl-2', 3'-O-(tetraisopropyldisiloxane-1,3-diyl)-α,αtrehalose (7) and 4,6,4',6'-di-O-benzylidene-2-O-palmitoyl-2', 3'-O-(tetraisopropyldisiloxane1,3-diyl)-α,α-trehalose (4) was dissolved in a mixed solvent of dry tetrahydrofuran (3 ml), dry acetonitrile (3 ml) and water (0.2 ml), and 1M tetrabutylammonium fluoride in tetrahydrofuran (1.6 ml) was added thereto. The mixture was allowed to react at room temperature for 1 hour and then chloroform (about 30 ml) was added thereto. The organic phase was successively washed with saturated aqueous ammonium chloride solution and water and dried over sodium sulfate. The inorganic salt was filtered off and the solvent was distilled off from the filtrate. The obtained residue was purified over a silicagel column (benzene:ethyl acetate=6:4) to give desilylated product (120 mg) in the form of white foamy solid.

The desilylated product (120 mg) was dissolved in acetic acid (30 ml), combined with water (2 ml), and the mixture was allowed to react at 90° C. for 1 hour. The solvent was distilled off from the reaction mixture, and again toluene was added to the residue, the solution was washed and toluene was distilled off (for the complete removal of acetic acid). The obtained residue was purified over a silicagel column (chloroform:methanol=7:3) to give 3-O-palmitoyl-α,α-trehalose (Ib-2) (43 mg, yield 19.0% based upon compound (3)) in the form of white solid, m.p. 109°-121° C.

Process iv

Reference Example iv-1

Preparation of 3,4,3',4'-di-O-(tetraisopropyldisiloxane-1,3-diyl)-6-O-trityl-α,α-trehalose (8)

Anhydrous α,α-trehalose (1) (2.15g, 6.3 millimole) was suspended in dry pyridine (90 ml), and 1,3-dichloro-1,1,3,3,-tetraisopropyldisiloxane (5.0 g, 15.8 millimole) in dry pyridine (30 ml) was added dropwise to the suspension and the mixture was allowed to react at room temperature for 24 hours. The solvent was distilled off from the reaction mixture, and water (300 ml) was added to the residue. The mixture was stirred for a while. The insoluble matter was filtered off and dried in a dessicator under vacuum. The obtained mass was washed with ether, filtered off, dried, dissolved in a developing solvent (chloroform:methanol=95:5) and purified over a silicagel column (chloroform:methanol=95:5). The first eluting colorless fractions were pooled, and the solvent was distilled off to give 4,6,4',6'-di-O-(tetraisopropyldisiloxane-1,3-diyl)- α,α-trehalose (2) (2.06 g, yield 40%) in the form of white solid, m.p. 222°-224° C.

A suspension of 4,6,4',6'-di-O-(tetraisopropyl-disiloxane-1,3-diyl)-α,α-trehalose (2)(2.05 g, 2.48 millimole) in dry N,N-dimethylformamide (120 ml) was warmed to 70° C. to dissolve, then pyridine hydrochloride (601.8 mg, 5.21 millimole) was added thereto. The mixture was allowed to react at room temperature for 72 hours. The solvent was distilled off from the reaction mixture, and the obtained residue was dissolved in chloroform. The organic phase was successively washed with saturated aqueous sodium bicarbonate and saturated sodium chloride solution, and dried over anhydrous sodium sulfate.

The solvent was distilled off from the filtrate. The residue was dissolved in a developing solvent (chloroform:methanol=95:5) and purified over a silicagel column (chloroform:methanol=95:5). The fast eluting fractions comprising impurities were discarded and the later colorless fractions were pooled, and the solvent was distilled off from the solution to give a mixture (1.14 g) of 3,4,3',4'-di-O-(tetraisopropyldisiloxane-1,3-diyl)-α,α-trehalose and other isomers.

The mixture (1.14 g) was dissolved in dry pyridine (10 ml) and combined with trityl chloride (786.2 mg, 2.82 millimole). The mixed solution was allowed to react at room temperature for 72 hours, and the solvent was distilled off therefrom. The residue was dissolved in benzene (some insoluble matter was present and filtered off), and purified over a silicagel column (benzene). The fast eluting fractions comprising impurities were discarded, and then the developing solvent was changed (bezene:ethyl acetate=95:5), and the colorless fractions from the second fraction were pooled. The solvent was distilled off to give 3,4,3',4'-di-O-(tetraisopropyldisiloxane-1,3-diyl)-6-O-trityl-α,α-trehalose (8) (508 mg) in the form of white foamy solid. The developing solvent was further changed (chloroform:methanol=95:5) and the compound before tritylation (as a mixture) was recovered and tritylated as described above to give 3,4,3',4'-di-O-(tetraisopropyldisiloxane-1,3-diyl)-6-O-trityl-α,α-trehalose (8), which was combined with already obtained product (773 mg, yield 51%), m.p. 68°–72° C.

Example iv-1

Preparation of 2,6'-di-O-decanoyl-α,α-trehalose (Ic-2)

To a solution of 3,4,3',4'-di-O-(tetraisopropyl-disiloxane-1,3-diyl)-6-O-trityl-α,α-trehalose (8) (200 mg, 0.19 millimole) and n-capric acid (86.1 mg, 0.49 millimole) dissolved in dry methylene chloride (8 ml) were added 4-dimethylaminopyridine (31.5 mg, 0.25 millimole) and N,N'-dicyclohexylcarbopyridine diimide (101.1 mg, 0.49 millimole) successively, and the mixture was allowed to react at room temperature for 21 hours. The precipitates formed in the reaction mixture were filtered off by suction, and the solvent was distilled off from the filtrate. The residue was dissolved in a developing solvent (n-hexane:ethyl acetate=9:1) (containing some insoluble mass), and purified over a silicagel column (n-hexane:ethyl acetate=9:1) to give 2,6'-di-O-decanoyl-3,4,3',4'-di-O-(tetraisopropyldisiloxane-1,3-diyl)-6-O-trityl-α,α-trehalose (9) (167.8 mg) as a mixture. The mixture was fractionated through thin layer chromatography (developing solvent: n-hexane:ethyl acetate=9:1) to give pure 2,6'-di-O-decanoyl-3,4,3',4'-di-O-(tetraisopropyldisiloxane-1,3-diyl)-6-O-trityl-α,α-trehalose (9) (119.5 mg).

Then, 2,6'-di-O-decanoyl-3,4,3',4'-di-O-(tetraisopropyl-disiloxane-1,3-diyl)-6-O-trityl-α,α-trehalose (9) (119.5 mg, 0.087 millimole) was dissolved in 1M tetrabutylammonium fluoride/tetrahydrofuran solution (3 ml), and the solution was allowed to react at room temperature for 30 minutes. The solvent was distilled off and the residue was dissolved in chloroform. The organic phase was successively washed with saturated aqueous ammonium chloride and water, and dried over anhydrous sodium sulfate. The solvent was distilled off and the residue was dissolved in a developing solvent (chloroform:methanol=9:1) and purified over a silicagel column (chloroform:methanol=9:1). The fast eluting fractions comprising impurities were discarded and pale yellow fractions were pooled, and the solvent was evaporated off from the pooled fractions to give the desilylated product, i.e., 2,6'-di-O-decanoyl-6-O-trityl-α,α-trehalose (10) (77.7 mg).

The viscous 2,6'-di-O-decanoyl-6-O-trityl-α,α-trehalose (10) was dissolved in dry ethanol (2 ml) and dry methylene chloride (2 ml), and combined with palladium black (150 mg). The mixture was hydrogenated at room temperature for 21 hours. The palladium black was filtered off and the solvent was distilled off. The residue was dissolved in a developing solvent (chloroform:methanol=8:2), and purified over a silicagel column (chloroform:methanol=8:2). The fast eluting fractions comprising impurities were discarded and colorless fractions were pooled. The solvent was removed from the solution to give 2,6'-di-O-decanoyl-α,α-trehalose (Ic-2) (20.2 mg, yield 17% started from (8)) in the form of white solid.

Example iv-2

Preparation of 2,6'-di-O-oleoyl-α,α-trehalose (Ic-5)

To a solution of 3,4,3',4'-di-O-(tetraisopropyldisiloxane-1,3-diyl)-6-O-trityl-α,α-trehalose (8) (300 mg, 0.28 millimole) dissolved in dry methylene chloride (8 ml) were added oleic acid (0.23 ml, 0.73 millimole), 4-demethylaminopyridine (41.5 mg, 0.34 millimole) and N,N'-dicyclohexylcarbodiimide (150.6 mg, 0.73 millimole) successively. The mixture was allowed to react at room temperature for 18 hours, and the formed precipitates were filtered off by suction, and the solvent was distilled off from the reaction mixture. The obtained residue was dissolved in a developing solvent (n-hexane:ethyl acetate=9:1) (containing some insoluble residue) and purified over a silicagel column (n-hexane:ethyl acetate=9:1) to give pure 2,6'-di-O-oleoyl-3,4,3',4'-di-O-(tetraisopropyldisiloxane-1,3-diyl)-6-O-trityl-α,α-trehalose (9) (144.1 mg).

Then 2,6'-di-O-oleoyl-3,4,3',4'-di-O-(tetraisopropyl-disiloxane-1,3-diyl)-6-O-trityl-α,α-trehalose (9) (144.1 mg, 0.09 millimole) was dissolved in 1M tetrabutylammonium fluoride/tetrahydrofuran solution (8 ml), and the solution was allowed to react at room temperature for 30 minutes. The solvent was distilled off and the residue was dissolved in chloroform, and then the organic phase was successively washed with saturated aqueous ammonium chloride and water, and dried over anhydrous sodium sulfate. The solvent was distilled off and the residue was dissolved in a developing solvent (chloroform:methanol=95:5), and purified over a silicagel column (chloroform:methanol=95:5) to give desilylated product of (9), 2,6'-di-O-oleoyl-6-O-trityl-α,α-trehalose (10) (100.2 mg).

The viscous product, 2,6'-di-O-decanoyl-6-O-trityl-α,α-trehalose (10), was dissolved in a mixed solvent of dry 1,2-dichloroethane (4 ml) and dry methanol (2 ml), and combined with p-toluenesulfonic acid monohydrate (5.7 mg, 0.03 millimole). The mixture was allowed to react at room temperature for 2 hours. The solvent was distilled off from the reaction mixture, and the residue was dissolved in a developing solvent (chloroform:methanol=8:2), and purified over a silicagel column (chloroform:methanol =8:2). The fast eluting fractions comprising impurities were discarded and the following colorless fractions were pooled. The solvent was distilled off to give 2,6'-di-O-oleoyl-α,α-trehalose (Ic-5) (34.2 mg, yield 14% based on (8)) in the form of colorless viscous product.

Example iv-3

Preparation of
2,6'-di-O-(9,10-epoxystearoyl)-α,α-trehalose (Ice-1)

To a solution of 70% m-chloroperbenzoic acid (61.6 mg, 0.25 millimole) dissolved in chloroform (6 ml) with ice cooling was added 2,6'-di-O-oleoyl-α,α-trehalose (Ic-5) (67.3 mg, 0.077 millimole) in chloroform (6 ml) dropwise under the same conditions. The mixture was allowed to warm to room temperature and to react for 4 hours. Chloroform (4 ml) was added to the reaction mixture, and the organic phase was successively washed with 10% aqueous sodium sulfite solution, saturated aqueous sodium bicarbonate solution, water and saturated aqueous sodium chloride solution and dried over sodium sulfate. The solvent was distilled off from the filtrate to give 2,6'-di-O-(9,10-epoxystearoyl)-α,α-trehalose (Ice-1) (41.7 mg, yield 8% started from (8)) in the form of colorless viscous product.

Example iv-4

Preparation of
2-O-oleoyl-6'-O-pentadecanoyl-α,α-trehalose (Ic-8)

A mixture of 3,4,3',4'-di-O-(tetraisopropyldisiloxane-1,3-diyl)-6-O-trityl-α,α-trehalose (8) (300 mg, 0.28 millimole) and n-pentadecanoic acid (82.4 mg, 0.34 millimole) was dissolved in dry methylene chloride (8 ml), and 4-dimethylaminopyridine (21.5 mg, 0.17 millimole) and N,N'-dicyclohexylcarbodiimide (70.2 mg, 0.34 millimole) were successively added thereto. The mixture was allowed to react at room temperature for 15 hours. The precipitates formed in the reaction mixture was filtered off by suction from the reaction mixture and the solvent were distilled off from the filtrate. The residue was dissolved in a developing solvent (n-hexane:ethylacetate=9:1) and purified over a silicagel column (n-hexane:ethylacetate=9:1). The fast eluting fractions comprising impurities were discarded. The latter colorless fractions were pooled and the solvent was distilled off to give 6'-O-pentadecanoyl-3,4,3',4'-di-O-(tetraisopropyldisiloxane-1,3-diyl)-6-O-trityl-α,α-trehalose (212 mg) in the form of white foamy solid. To a solution of 6'-O-pentadecanoyl-3,4,3',4'-di-O-(tetraisopropyldisiloxane-1,3-diyl)-6-O-trityl-α,α-trehalose (212 mg, 0.16millimole) dissolved in dry methylene chloride (8 ml) were added oleic acid (0.06 ml, 0.19 millimole), 4-dimethylaminopyridine (12.3 mg, 0.1 millimole) and N,N'-dicyclohexylcarbodiimide (39.2 mg, 0.19 millimole) successively and the mixture was allowed to react at room temperature for 19 hours. The precipitates formed in the reaction mixture was filtered off by suction and the solvent was distilled off from the filtrate. The residue was dissolved in a developing solvent (n-hexane:ethyl acetate=9:1) (containing some insoluble mass) and purified over a silicagel column (n-hexane:ethyl acetate=9:1) to give 2-O-oleoyl -6'-O-pentadecanoyl-3,4,3',4'-di-O-(tetraisopropyldisiloxane-1,3-diyl)-6-O-trityl-α,α-trehalose (9) (104.7 mg) as a mixture. The mixture was fractionated through thin layer chromatography (a developing solvent; n-hexane:ethyl acetate=9:1) to give pure 2-O-oleoyl-6'-O-pentadecanoyl3,4,3',4'-di-O-(tetraisopropyldisiloxane-1,3-diyl)-6-O-trityl-α,α-trehalose (9) in the form of colorless viscous pure product (77.9 mg).

Then, 2-O-oleoyl-6'-O-pentadecanoyl-3,4,3',4'-di-O-(tetraisopropyldisiloxane-1,3-diyl)-6-O-trityl-α,α-trehalose (9) (77.9mg, 0.05 millimole) was dissolved in 1M tetrabutylammonium fluoride/tetrahydrofuran solution (4 ml) and the mixture was allowed to react at room temperature for 30 minutes. The solvent was distilled off from the reaction mixture and chloroform was added to dissolve the residue. The organic phase was successively washed with saturated aqueous ammonium chloride solution and water and dried over sodium sulfate. The solvent was distilled off. The obtained residue was dissolved in a developing solvent (chloroform:methanol=95:5), and purified over a silicagel column (chloroform:methanol=95:5). The fractions comprising impurities were discarded and colorless fractions were pooled. The solvent was distilled off to give desilylated product 2-O-oleoyl-6'-O-pentadecanoyl-6-O-trityl-α,α-trehalose (10) (53.7 mg). The obtained 2-O-oleoyl-6'-O-pentadecanoyl-6-O-trityl-α,α-trehalose (10) was dissolved in a mixed solvent of dry 1,2-dichloroethane (4 ml) and dry methanol (2 ml) and combined with p-toluenesulfonic acid monohydrate (9.51 mg, 0.05 millimole). The mixture was allowed to react at room temperature for 2 hours. The solvent was distilled off from the reaction mixture. The residue was dissolved in a developing solvent (chloroform:methanol=8:2) and purified over a silicagel column (chloroform:methanol=8:2). The fast eluting fractions comprising impurities were discarded and colorless fractions were pooled. The solvent was distilled off to give 2-O-oleoyl-6'-O-pentadecanoyl-α,α-trehalose (Ic-8) (21.7 mg, yield 10% based on (8)) in the form of colorless viscous product.

Example iv-5

Preparation of
6'-O-corynomycoloyl-2-O-pentadecanoyl-α,α-trehalose (Ic-9)

To a solution of 3,4,3',4'-di-O-(tetraisopropyl-disiloxane-1,3-diyl)-6-O-trityl-α,α-trehalose (8) (300 mg, 0.28 millimole) dissolved in dry methylene chloride (5 ml) were added 3-O-benzylcorynomycolic acid (328.7 mg, 0.56 millimole) in dry methylene chloride (3 ml), 4-dimethylaminopyridine (34.6 mg, 0.28 millimole) and N,N'-dicyclohexylcarbodiimide (117.9 mg, 0.56 millimole) successively, and the mixture was allowed to react at room temperature for 23 hours. The precipitates formed in the reaction mixture were filtered off by suction, and the solvent was distilled off from the filtrate. The residue was dissolved in a developing solvent (n-hexane:ethyl acetate=9:1) (containing some insoluble mass) and purified over a silicagel column (n-hexane:ethyl acetate=9:1). The fast eluting fractions comprising impurities were discarded and colorless fractions were pooled. The solvent was distilled off to give 6'-O-(3-O-benzylcorynomycoloyl)-3,4,3',4'-di-O-(tetraisopropyldisiloxane-1,3-diyl)-6-O-trityl- α,α-trehalose (458.8 mg) in the form of white viscous product. The obtained 6'-O-(3-O-benzyl-corynomycoloyl)3,4,3',4'-di-O-(tetraisopropyldisiloxane-1,3-diyl)-6-O-trityl- α,α-trehalose was dissolved in dry methylene chloride (8 ml) and n-pentadecanoic acid (101.8 mg, 0.42 millimole), 4-dimethylaminopyridine (34.6 mg, 0.28 millimole) and N,N'-dicyclohexylcarbodiimide (86.7 mg, 0.42 millimole) were successively added thereto, and then the mixture was allowed to react at room temperature for 19.5 hours. The precipitates formed in the reaction mixture was filtered off by suction and the solvent was distilled off from the filtrate. The residue was dissolved in a developing solvent (n-hexane:ethyl acetate=95:5) and purified over a silicagel column (n-hexane:ethyl acetate=95:5) to give 6'-O-(3-O-benzyl-corynomycoloyl)-2-O-pentadecanoyl-3,4,3',4'-di-O-(tetraisopropyldisiloxane-1,3-diyl)-6-O-trityl-α,α-trehalose as a mixture. The mixture was fractionated through thin layer chromatography (a developing solvent:n-hexane:ethyl acetate=95:5) to give pure 6'-O-(3-O-benzyl-corynomycoloyl)-2-O-pentadecanoyl-3,4,3',4'-di-O-(tetraisopropyldisiloxane-1,3-diyl)-6-O-trityl-α,α-trehalose (9) (229.4 mg) in the form of colorless viscous product.

Then, 6'-O-(3-O-benzyl-corynomycoloyl)-2-O-pentadecanoyl-3,4,3',4'-di-O-(tetraisopropyldisiloxane-1,3-diyl)-6-O-trityl-α,αtrehalose (9) (229.4 mg, 0.123 millimole) was dissolved in 1M tetrabutylammonium fluoride in tetrahydrofuran solution (8 ml) and the mixture was allowed to react at room temperature for 30 minutes. The solvent was distilled off from the reaction mixture and the obtained residue was dissolved in chloroform. The organic phase was successively washed with saturated aqueous ammonium chloride solution and water and dried over sodium sulfate. The solvent was distilled off and the residue was dissolved in a developing solvent (chloroform:methanol=95:5) and purified over a silicagel chromatography (chloroform:methanol=95:5). The fast eluting fractions comprising impurities were discarded and colorless fractions were pooled. The solvent was distilled off to give the desilylated product, i.e. 6'-O-(3-O-benzyl-corynomycoloyl)-2-O-pentadecanoyl-6-O-trityl-α,α-trehalose (10) (169.5 mg). The obtained 6'-O-(3-O-benzyl-corynomycoloyl)-2-O-pentadecanoyl-6-O-trityl-α,α-trehalose was dissolved in a mixed solvent of dry methylene chloride (3 ml) and dry ethanol (3 ml), and the mixture was hydrogenated over palladium black (169.5 mg) at room temperature for 15 hours. The palladium black was filtered off from the reaction mixture and the solvent was distilled off from the filtrate. The residue was dissolved in a developing solvent (chloroform:methanol=9:1) and fractionated over a silicagel column (chloroform:methanol=9:1). The fast eluting fractions comprising impurities were discarded and colorless fractions were pooled. The solvent was distilled off to give 6'-O-corynomycoloyl-2-O-pentadecanoyl-α,α-trehalose (Ic-9) (81.4 mg, yield 28%) in the white foamy solid.

Example iv-6

Preparation of
6'-O-(3-hydroxy-2-n-tetradecyl-11-icosenoyl)-2-O-pentadecanoyl-α,α-trehalose (Ic-13)

To a solution of 3,4,3',4'-di-O-(tetraisopropyldisiloxane-1,3-diyl)-6-O-trityl-α,α-trehalose (8) (500 mg, 0.467 millimole) dissolved in dry methylene chloride (5 ml) were added 3-(t-butyldimethylsilyloxy)-2-n-tetradecyl-1licosenoic acid (387.2 mg, 0.607 millimole) in dry methylene chloride (2 ml), 4-dimethylaminopyridine (37.1 mg, 0.304 millimole) and N,N'-dicyclohexylcarbodiimide (125.4 mg, 0.607 millimole) successively and the mixture was allowed to react at room temperature for 23 hours. The precipitates formed in the reaction mixture were filtered off by suction and the solvent was distilled off from the filtrate. The residue was dissolved in a developing solvent (n-hexane:ethyl acetate=93:7) and purified over a silicagel column (n-hexane:ethyl acetate=93:7). The fast eluting fractions comprising impurities were discarded and colorless fractions were pooled. The solvent was distilled off to give 6'-O-]3-(t-butyldimethylsilyloxy)-2-n-tetradecyl-11-icosenoyl]-3,4,3 ',4'-di-O-(tetraisopropyldisiloxane-1,3-diyl)-6-O-trityl-α,α-trehalose (580 mg)in the form of colorless viscous product. Then, 6'-O-3-(t-butyldimethylsilyloxy)-2-n-tetradecyl-11-icosenoyl]-3,4,3',4'-di-O-(tetraisopropyl-disiloxane-1,3-diyl)-6-O-trityl-α,α-trehalose was dissolved in dry methylene chloride (7 ml) and n-pentadecanoic acid (125 mg, 0.515 millimole), 4-dimethylaminopyridine (31.5 mg, 0.258 millimole) and N,N'-dicyclohexylcarbodiimide (106 mg, 0.515 millimole) were successively added thereto. The mixture was allowed to react at room temperature for 39 hours. The precipitates formed in the reaction mixture was filtered off by suction and the solvent was distilled off from the filtrate. The residue was dissolved in a developing solvent (n-hexane:ethyl acetate=95:5) and purified over a silicagel column (n-hexane:ethyl acetate=95:5). The fast eluting fractions comprising impurities were discarded and colorless fractions were pooled and the solvent was distilled off. The obtained viscous product was again fractionated through preparative TLC (a developing solvent; n-hexane:ethyl acetate=9:1) to give 6'-O-[3-(t-butyldimethylsilyloxy)-2-n-tetradecyl-11-icosenoyl]-2-O-pentadecanoyl-3,4,3',4'-di-O-(tetraisopropyldisiloxane-1,3-diyl)6-O-trityl-α,α-trehalose (9) (470 mg) as a mixture. The mixture (9) (470 mg) was dissolved in a mixture of dry tetrahydrofuran (10 ml), dry acetonitrile (10 ml) and water (1 ml), and 1M tetrabutylammonium fluoride in tetrahydrofuran (5 ml) was added thereto. The mixture was allowed to react at room temperature for 1.5 hours and combined with chloroform (100 ml). The mixture was washed with water and dried over anhydrous sodium sulfate. The inorganic salt was filtered off and the solvent was distilled off from the filtrate. The residue was dissolved in a developing solvent (chloroform:methanol=95:5) and was purified over a silicagel column (chloroform:methanol=95:5). The fast eluting solution comprising impurities were discarded and colorless fractions were pooled. The solvent was distilled off to give pure 6'-O-[3-(t-butyldimethylsilyloxy)-2-n-tetradecyl-11-icosenoyl-]2-O-pentadecanoyl-6-O-trityl-α,α-trehalose (10) (200 mg) in the form of white viscous foam. Then, 6'-O-[3-(t-butyldimethylsilyloxy)-2-n-tetradecyl-11-icosenoyl]-2-O-pentadecanoyl-6-O-trityl-α,α-trehalose (10) was dissolved in acetic acid (50 ml) and water (5.0 ml) was added thereto. The mixture was allowed to react at 90° C. for 1 hour. and the solvent was distilled off from the reaction mixture. The residue was dissolved in a developing solvent (chloroform:methanol=9:1) and purified over a silicagel column (chloroform:methanol=9:1). The fast eluting solution comprising impurities were discarded and colorless fractions were pooled. The solvent was distilled off to give 6'-O-(3-hydroxy-2-n-tetradecyl-11-icosenoyl)-2-O-pentadecanoyl-α,α-trehalose (Ic-13) (85 mg, yield 17.0%) in the form of white waxy solid.

As the other compounds (Ic) according to this invention, the following compounds were prepared as described in either of the above Examples (from Example iv-1 to Example iv-6).

2,6'-Di-O-hexanoyl-α,α-trehalose (Ic-1),
2,6'-Di-O-pentadecanoyl-α,α-trehalose (Ic-3),
2,6'-Di-O-icosanoyl-α,α-trehalose (Ic-4),
2,6'-Di-O-(9,12-octadecadienoyl)-α,α-trehalose (Ic-6),
2,6'-Di-O-corynomycoloyl-α,α-trehalose (Ic-7),
6'-O-(3-Hydroxy-2-tetradecyl-docosanoyl)2-O-pentadecanoyl-α,α-trehalose (Ic-10), 2-O-(9,12-Octadecadienoyl)-6'-O-oleoyl-α,α-trehalose (Ic-11)

6'-O-Palmitoyl-2-O-pentadecanoyl-α,α-trehalose (Ic-12)

6'-O-(3-Hydroxy-2-tetradecyl-11-icosenoyl)-2-O-oleoyl-α,αtrehalose (Ic-14)

2-O-Oleoyl-6'-O-retinoyl-α,α-trehalose (Ic-15)

Process v

Reference Example v-1

Preparation of 4,6,4',6'-di-O-benzylidene-2,3-di-O-oleoyl-2',3'-O-(tetraisopropyldisiloxane-1,3-diyl)-α,αtrehalose (11)

To a solution of 4,6,4',6'-di-O-benzylidene-2,3-O-(tetraisopropyldisiloxane-1,3-diyl)-α,α-trehalose (3) (1.0 g, 1.31 millimole) dissolved in dry methylene chloride (31.6 ml) were added oleic acid (1.01 ml, 3.15 millimole), 4-dimethylaminopyridine (193 mg, 1.58 millimole) and N-N'-dicyclohexylcarbodiimide (650 mg, 3.15 millimole) successively and the mixture was allowed to react at room temperature for 15 hours. The insoluble matter formed in the reaction mixture was filtered off by suction and the solvent was distilled off from the filtrate. The residue was purified over a silicagel column (benzene) to give 4,6,4',6'-di-O-benzylidene-2,3-di-O-oleoyl-2', 3'-O-(tetraisopropyldisiloxane-1,3-diyl)-α,α-trehalose (11) (1.61 g, yield 95.2%) in the form of colorless oil.

Example v-2

Preparation of 2,3-di-O-oleoyl-α,α-trehalose (Id-1)

To a solution of 4,6,4',6'-di-O-benzylidene-2,3-di-O-oleoyl-2', 3'-O-(tetraisopropyldisiloxane-1,3-diyl)-α,α-trehalose (11) (355.6 mg, 0.276 millimole) dissolved in a mixed solvent of dry tetrahydrofuran (13.2 ml), dry acetonitrile (13.2 ml) and water (1.32 ml) was added 1M tetrabutylammonium fluoride in tetrahydrofuran (2.76 ml). The mixture was allowed to react at room temperature for 2 hours and combined with chloroform (200 ml). The mixture was washed with water and dried over anhydrous sodium sulfate. The inorganic salt was filtered off and the solvent was distilled off from the filtrate. The residue was purified over a silicagel column (benzene:ethyl acetate=7:3) to give desilylated product (275.1 mg) in the form of white viscous foam.

The desilylated product (245.8 mg) was dissolved in acetic acid (44.4 ml) and water (4.9 ml) was added thereto. The mixture was allowed to react at 90° C. for 1 hour, and the solvent was distilled off from the reaction mixture. The residue was purified over a silicagel column (chloroform:methanol=8:2) to give 2,3-di-O-oleoyl-α,α-trehalose (Id-1) (143.5 mg, yield 66.8%) in the form of white viscous foam, m.p. 102°–113° C.

The compounds (Id), i.e. 2,3-di-O-pentadecanoyl-α,α-trehalose (Id-5), 2,3-di-O-(12-hydroxy-stearoyl)-α,α-trehalose (Id-9) and 2,3-di-O-(9,12-octadecadienoyl)-α,α-trehalose (Id-12) shown in the Table 1 were prepared as described in the above Examples.

Example v-3

Preparation of 2,3-di-O-(9,10-epoxystearoyl)-α,α-trehalose (Ide-1)

A solution of 2,3-di-O-oleoyl-α,α-trehalose (Id) (69.7 mg, 0.08 millimole) in chloroform (6 ml) was added dropwise to m-chloroperbenzoic acid (64.1 mg, 0.26 millimole) in chloroform (6 ml) with ice cooling and the mixture was allowed to warm to room temperature and to react for 4 hours. Chloroform (40 ml) was added thereto. The reaction mixture was successively washed with 10% sodium sulfite solution, saturated aqueous sodium bicarbonate solution, water and saturated aqueous sodium chloride solution and then was dried over anhydrous sodium sulfate. The inorganic salt was filtered off and the solvent was removed from the filtrate. The residue was fractionated through preparative TLC (benzene:ethyl acetate=6:4) and was extracted with a mixed solvent (chloroform:methanol=8:2). The solvent was distilled off to give 2,3-di-O-(9,10-epoxystearoyl)-α,α-trehalose (Ide-1) (44.3 mg, yield 61.3%) in the form of white waxy solid.

Process vi

Reference Example vi-1

Preparation of 4,6,4',6'-di-O-benzylidene-3-O-(9,12-octadecadinoyl)-2-O-oleoyl-2', 3'-O-(tetraisopropyldisiloxane-1,3-diyl)-α,α-trehalose (11)

To a solution of 4,6,4',6'-di-O-benzylidene-2-O-oleoyl-2', 3'-O-(tetraisopropyldisiloxane-1,3-diyl)-α,α-trehalose (4) (152.9 mg, 0.149 millimole) dissolved in dry methylene chloride (1.8 ml) were added linoleic acid (0.056 ml, 0.179 millimole), 4-dimethylaminopyridine (10.9 mg, 0.085 millimole) and N,N'-dicyclohexylcarbodiimide (36.9 mg, 0.179 millimole) successively and the mixture was allowed to react at room temperature for 2.5 hours. The solvent was distilled off from the reaction mixture and the obtained residue was purified over a silicagel column (n-hexane:ethyl acetate=85:15) to give 4,6,4',6'-di-O-benzylidene-3-O-(9,12-octadecadienoyl)-2-O-oleoyl-2', 3'-O-(tetraisopropyldisiloxane-1,3-diyl)-α,α-trehalose (11) (191.9 mg, quantitative) in the form of colorless oil.

Example vi-1

Preparation of 3-O-(9,12-octadecadienoyl)-2-O-oleoyl-α,α-trehalose (Id-2)

To a solution of 4,6,4',6'-di-O-benzylidene-3-O-(9,12-octadecadienoyl)-2-O-oleoyl-2', 3'-O-(tetraisopropyldisiloxane-1,3-diyl)-α,α-trehalose (11) (160.8 mg, 0.125 millimole) dissolved in a mixed solvent of dry tetrahydrofuran (6 ml), dry acetonitrile (6 ml) and water (0.59 ml), were added 1M tetrabutylammonium fluoride in tetrahydrofuran (1.25 ml). The mixture was allowed to react at room temperature for 2 hours and combined with chloroform (about 100 ml). The mixture was successively washed with saturated aqueous ammonium chloride solution and water and dried over anhydrous sodium sulfate. The inorganic salt was filtered off and the solvent was distilled off from the filtrate. The residue was purified over a silicagel column (n-hexane:ethyl acetate=6:4) to give desilylated product (119.2 mg) in the form of white waxy solid.

The desilylated product (116.8 mg) was dissolved in acetic acid (21.1 ml) and water (2.3 ml) was added thereto. The mixture was allowed to react at 90° C. for 1 hour and the solvent was distilled off from the reaction mixture. The residue was purified over a silicagel column (chloroform:methanol=85:15) to give 3-O-(9,12-octadecadienoyl)-2-O-oleoyl-α,α-trehalose (Id-2)

(72.2 mg, yield 66.5%) in the form of colorless glassy solid, m.p. 85°–114° C.

The compounds (Id) shown in the Table 1, i.e. 3-O-stearoyl-2-O-pentadecanoyl-α,α-trehalose (Id-4), 3-O-oleoyl-2-O-pentadecanoyl-α,α-trehalose (Id-6), 2-O-(12-hydroxy-stearoyl)-3-O-pentadecanoyl-α,α-trehalose (Id-8), 2-O-(12-hydroxy-stearoyl)-3-O-(2-octyl-cyclopropane-octanoyl)-α,α-trehalose (Id-10) and 2-O-(12-hydroxy-stearoyl)-3-O-oleoyl-α,α-trehalose (Id-11) were prepared as described in the above Examples.

Process vii

Reference example vii-1

Preparation of 2,3-di-O-(3-O-benzylcorynomycoloyl)-4,6,4',6'-di-O-benzylidene-2', 3'-O-(tetraisopropyldisiloxane-1,3-diyl)-α,α-trehalose (11)

To a solution of 3-O-(3-O-benzylcorynomycoloyl)-4,6,4',6'-di-O-benzylidene-2', 3'-O-(tetraisopropyldisiloxane-1,3-diyl)-α,α-trehalose (7) (100 mg, 75.2 micromole) dissolved in dry methylene chloride (1.5 ml) were added 3-O-benzylcorynomycolic acid (88 mg, 150.4 micromole), 4-dimethylaminopyridine (9 mg, 75.2 micromole) and N,N'-dicyclohexylcarbodiimide (31 mg, 150.4 micromole) successively. The mixture was allowed to react under reflux for 17 hours. The solvent was distilled off from the reaction mixture and the residue was purified over a silicagel column (n-hexane:ether=7:3 followed by toluene) to give 2,3-di-O-(3-O-benzylcorynomycoloyl)-4,6,4',6'-di-O-benzylidene-2', 3'-O- tetraisopropyldisiloxane-1,3-diyl)-α,α-trehalose (11) (24 mg, yield 16.9%) in the form of colorless oil.

Example vii-1

Preparation of 2,3-di-O-corynomycoloyl-α,α-trehalose (Id-3)

To a solution of 2,3-di-O-(3-O-benzylcorynomycoloyl)4,6,4',6'-di-O-benzylidene-2', 3'-O-(tetraisopropyldisiloxane-1,3-diyl)-α,α-trehalose (11) (24 mg, 12.7 micromole) dissolved in a mixed solvent of dry tetrahydrofuran (1 ml), dry acetonitrile (0.6 ml) and water (0.06 ml), were added 1M tetrabutylammonium fluoride in tetrahydrofuran (0.13 ml). The mixture was allowed to react at room temperature for 1 hour and combined with chloroform (30 ml). The mixture was washed with water and dried over anhydrous sodium sulfate. The inorganic salt was filtered off and the solvent was distilled off from the filtrate. The residue was purified over a silicagel column (toluene:ethyl acetate=78:22) to give desilylated product (16 mg) in the form of colorless oil.

The desilylated product (16 mg) was dissolved in a mixed solvent of dry methylene chloride (1 ml) and dry methanol (1 ml) and the mixture was combined with palladium black (16 mg) and hydrogenated at room temperature for 16 hours. The palladium black was filtered off from the reaction mixture and the solvent was distilled off from the filtrate. The residue was purified over a silicagel column (chloroform:methanol=85:15) to give 2,3-di-O-corynomycoloyl-α,α-trehalose (Id-3) (11.2 mg, yield 68.2%), m.p. 159°–163° C., in the form of white waxy solid.

The compounds (Id-3) in the following Table 1, i.e. 3-O-corynomycoloyl-2-O-pentadecanoyl-α,α-trehalose (Id-7) was prepared as described in the above Examples.

Process viii

Reference Example viii-1

Preparation of 2,3-di-O-oleoyl-2', 3'-O-(tetraisopropyldisiloxane-1,3-diyl)-α,α-trehalose (12)

To a solution of 4,6,4',6'-di-O-benzylidene-2,3-di-O-oleoyl-2', 3'-O-(tetraisopropyldisiloxane-1,3-diyl)-α,α-trehalose (11) (1.65 g, 1.28 millimole) dissolved in acetic acid (290 ml) was added water (14.5 ml) and the mixture was allowed to react at 90° C. for 1 hour. The solvent was distilled off from the reaction mixture and toluene was added to the residue and distilled off in order to completely remove acetic acid. The residue was purified over a silicagel column (benzene:ethyl acetate=65:35) to give 2,3-di-O-oleoyl-2', 3'-O-(tetraisopropyldisiloxane-1,3-diyl)-α,α-trehalose (12) (1.07 mg, yield 75.4%) in the form of white viscous foam.

Example viii-2

Preparation of 2,3-di-O-oleoyl-2', 3'-O-(tetraisopropyldisiloxane-1,3-diyl)-6-O-trityl-α,α-trehalose (13)

A solution of 2,3-di-O-oleoyl-2', 3'-O-(tetraisopropyldisiloxane-1,3-diyl)-α,α-trehalose (12) (1.07 g, 0.96 millimole) dissolved in dry pyridine (16.6 ml) was combined with trityl chloride (482 mg, 1.73 millimole) and the mixture was allowed to react at room temperature for 87 hours (an additional trityl chloride (268 mg, 0.96 millimole) being added after 24 hours). The solvent was distilled off from the reaction mixture and benzene was added to the residue. The insoluble matter (trityl chloride) was filtered off by suction. The filtrate was purified over a silicagel column (benzene→ benzene:ethyl acetate=95:5) repurified over a silicagel column (n-hexane:ether=1:1) to give 2,3-di-O-oleoyl-2', 3'-O-(tetraisopropyldisiloxane-1,3-diyl)-6-O-trityl-α,α-trehalose (13) (385 mg, yield 30%) in the form of colorless viscous product.

Reference Example viii-3

Preparation of 6'-O-(2-octyl-cyclopropane-octanoyl)-2,3-di-O-oleoyl-2', 3'-O-(tetraisopropyldisiloxane-1,3-diyl)-6-O-trityl-α,α-trehalose (14)

To a solution of 2,3-di-O-oleoyl-2',3'-O-(tetraisopropyldisiloxane-1,3-diyl)-6-O-trityl-α,α-trehalose (13) (425mg, 0.313 millimole) dissolved in dry methylene chloride (5 ml) were added 2-octyl-cyclopropane-octanoic acid (111.5 mg, 0.376 millimole) in dry methylene chloride (1 ml), 4-dimethylaminopyridine (23.2 mg, 0.188 millimole) and N,N'-dicyclohexylcarbodiimide (77.6 mg, 0.376 millimole) successively and the mixture was allowed to react at room temperature for 17 hours. The insoluble matter in the reaction mixture was filtered off by suction and the solvent was distilled off from the filtrate. The residue was purified over a silicagel column (benzene) to give 6'-O-(2-octyl-cyclopropane-octanoyl)-2,3-di-O-oleoyl-2', 3'-O-(tetraisopropyldisiloxane-1,3-diyl)-6-O-trityl-α,α-trehalose (14) in the form of colorless viscous product.

Reference Example viii-4

Preparation of
6'-O-[3-(t-butyl-dimethylsilyloxy)-2-n-tetradecyl-11-icosenoyl]-2,3-di-O-oleoyl-2',3'-O-(tetraisopropyl-disiloxane-1,3-diyl)-6-O-trityl-α,α-trehalose (14)

To a solution of 2,3-di-O-oleoyl-2', 3'-O-(tetraisopropyldisiloxane-1,3-diyl)-6-O-trityl-α,α-trehalose (13) (385 mg, 0.28 millimole) dissolved in dry methylene chloride (2 ml) were added 3-(t-butyl-dimethylsilyloxy)-2-n-tetradecyl-11-icosenoic acid (250 mg, 0.39 millimole) in dry methylene chloride (3 ml), 4-dimethylaminopyridine (22.5 mg, 0.18 millimole) and N,N'-dicyclohexylcarbodiimide (76.2 mg, 0.37 millimole) successively and the mixture was allowed to react at room temperature for 16 hours. The solvent was distilled off and the residue was purified over a silicagel column (n-hexane:ethyl acetate=9:1) to give 6'-O-[3-(t-butyl-dimethylsilyloxy)-2-n-tetradecyl-11-icosenoyl]-2,3-di-O-oleoyl-2', 3'-O-(tetraisopropyldisiloxane-1,3-diyl)-6-O-trityl-α,α-trehalose (14) (394 mg, yield 70.3%) in the form of colorless viscous product.

Example viii-1

Preparation of
6'-O-(2-octyl-cyclopropane-octanoyl)-2,3-di-O-oleoyl-α,α-trehalose (Ie-1)

To a solution of 6'-O-(2-Octyl-cyclopropane-octanoyl)-2,3-di-O-oleoyl-2', 3'-O-(tetraisopropyl-disiloxane-1,3-diyl)-6-O-trityl-α,α-trehalose (14) (420 mg, as a mixture) dissolved in a mixed solvent of dry tetrahydrofuran (5 ml), dry acetonitrile (5 ml) and water (1 ml) was added 1M tetrabutylammonium fluoride in tetrahydrofuran (2.5 ml). The mixture was allowed to react at room temperature for 1 hour combined with chloroform (50 ml). The mixture was successively washed with saturated ammonium chloride solution and water and dried over anhydrous sodium sulfate. The inorganic salt was filtered off and the solvent was distilled off from the filtrate. The residue was purified over a silicagel column (n-hexane:ethyl acetate=1:1) to give the desilylated product (305 mg) in the form of white viscous foam.

The desilylated product (305 mg) was dissolved in a mixed solvent of dry 1,2-dichloroethane (8 ml) and dry methanol (4 ml), and combined with p-toluenesufonic acid monohydrate (41.8 mg, 0.22 millimole). The mixture was allowed to react at room temperature for 1 hour and the solvent was distilled off from the reaction mixture. The residue was purified over a silicagel column (chloroform:methanol=9:1) to give 6'-O-(2-octyl-cyclopropane-octanoyl)-2,3-di-O-oleoyl-α,α-trehalose (Ie-1) (175 mg, yield 48.6% started from compound (13)) in the form of white viscous foam.

The compounds (Ie) in the Table 1, i.e. 2,3-di-O-oleoyl-6'-O-pentadecanoyl-α,α-trehalose (Ie-7) was prepared as described in the above Examples.

Example viii-2

Preparation
6'-O-(3-hydroxy-2-n-tetradecyl-11-icosenoyl)-2,3-di-O-oleoyl-α,α-trehalose (Ie-2)

To a solution of 6'-O-[3-(t-butyl-dimethylsilyloxy)-2-n-tetradecyl-11-icosenoyl]-2,3-di-O-oleoyl-2', 3'-O-(tetraisopropyldisiloxane-1,3-diyl)-6-O-trityl-α,α-trehalose (14) (390 mg, 0.197 millimole) dissolved in a mixed solvent of dry tetrahydrofuran (9.6 ml), dry acetonitrile (9.6 ml) and water (0.96 ml) was added 1M tetrabutylammonium fluoride in tetrahydrofuran (1.9 ml). The mixture was allowed to react at room temperature for 1 hour and combined with chloroform (about 100 ml). The mixture was washed with water and dried over anhydrous sodium sulfate. The inorganic salt was filtered off and the solvent was distilled off from the filtrate. The residue was purified over a silicagel column (benzene:ethyl acetate=6:4) to give desilylated product (292 mg) in the form of white viscous foam.

The desilylated product (292 mg, 0.167 millimole) was dissolved in acetic acid (52.7 ml) and water (5.9 ml) was added thereto. The mixture was allowed to react at 90° C. for 1 hour and the solvent was distilled off from the reaction mixture. The residue was purified over a silicagel column (chloroform:methanol=98:2) to give 6'-O-(3-hydroxy-2-n-tetradecyl-11-icosenoyl)-2,3-di-O-oleoyl-α,α-trehalose (Ie-2) (110 mg, yield 40.8%) in the form of white waxy solid, m.p. 85° 90° C.

The compounds (Ie) in the Table 1, i.e. 2,3,6'-tri-O-pentadecanoyl-α,α-trehalose (Ie-4), 2,3,6'-tri-O-(9,12-octadecadienoyl)-α,α-trehalose (Ie-5) and 2,3-di-O-pentadecanoyl-6'-O-oleoyl-α,α-trehalose (Ie-6) were prepared as described in the above Examples.

Process ix

Reference Example ix-1

Preparation of
4,6,4',6'-di-O-benzylidene-2-O-pentadecanoyl-2', 3'-O-(tetraisopropyldisiloxane-1,3diyl)-α,α-trehalose (4)

To a solution of 4,6,4',6'-di-O-benzylidene-2', 3'-O-(tetraisopropyldisiloxane-1,3-diyl)-α,α-trehalose (3) (100 mg, 0.13 millimole) dissolved in dry methylene chloride (3 ml) under argon atomsphere were added pentadecanoic acid (38 mg, 0.158 millimole), 4-dimethylaminopyridine (10 mg, 0.079 millimole) and N,N'-dicyclohexylcarbodiimide (32 mg, 0.158 millimole) successively and the mixture was allowed to react at room temperature for 18.5 hours. The solvent was distilled off from the filtrate and the residue was purified over a silicagel column (benzene:ethyl acetate=95:5) to give 4,6,4',6'-di-O-benzylidene- 2-O-pentadecanoyl-2', 3'-O-(tetraisopropyldisiloxane-1,3-diyl)-α,α-trehalose (4) (118mg, yield 92.5%) in the form of colorless oil.

Reference Example ix-2

Preparation of
4,6,4',6'-di-O-benzylidene-2-O-pentadecanoyl-3-O-stearoyl-2', 3'-O-(tetraisopropyldisiloxane-1,3 diyl)-α,α-trehalose (11)

To a solution of 4,6,4',6'-di-O-benzylidene-2 -O-pentadecanoyl-2', 3'-O-(tetraisopropyldisiloxane-1,3-diyl)-α,α-trehalose (4) (408 mg, 0.414 millimole) dissolved in dry methylene chloride (6 ml) under argon atomosphere were added stearic acid (141.3 mg, 0.498 millimole), 4-dimethylaminopyridine (30.3 mg, 0.248 millimole) and N,N'-dicyclohexylcarbodiimide (102.5 mg, 0.498 millimole) successively and the mixture was allowed to react at room temperature for 3.5 hours. The solvent was distilled off from the reaction mixture and the residue was purified over a silicagel column (benzene) to give 4,6,4',6'-di-O-benzylidene-2-O-pentadecanoyl-3-O-stearoyl-2', 3'-O-(tetraisopropyldisiloxane-1,3-diyl)-α,α-trehalose (11) (433 mg, yield 87.7%) in the form of colorless viscous product.

Reference Example ix-3

Preparation of 2-O-pentadecanoyl-3-O-stearoyl-2', 3'-O-(tetraisopropyldisiloxane-1,3-diyl)-α,α-trehalose (12)

A solution of 4,6,4',6'-di-O-benzylidene-2-O-pentadecanoyl-3-O-stearoyl-2', 3'-O-(tetraisopropyldisiloxane-1,3-diyl)-α,α-trehalose (11) (910 mg, 0.76 millimole) dissolved in acetic acid (143.8 ml) was combined with water (8.6 ml) and the mixture was allowed to react at 90° C. for 1 hour. The solvent was distilled off from the reaction mixture and the residue was purified over a silicagel column (benzene:ethyl acetate=8:2→ benzene:ethyl acetate=65:35) to give 2-O-pentadecanoyl-3-O-stearoyl-2', 3'-O-(tetraisopropyldisiloxane-1,3-diyl)-α,α-trehalose (12) (600 mg, yield 73.2%) in the form of colorless viscous foamy product.

Example ix-6

Preparation of 2-O-pentadecanoyl-3-O-stearoyl-2', 3'-O-(tetraisopropyldisiloxane-1,3-diyl)-6-O-trityl-α,α-trehalose (13)

A solution of 2-O-pentadecanoyl-3-O-stearoyl-2', 3'-O-(tetraisopropyldisiloxane-1,3-diyl)-α,α-trehalose (12) (560 mg, 0.52 millimole) dissolved in dry pyridine (9 ml) was combined with trityl chloride (261.2 mg 0.94 millimole) and the mixture was allowed to react at room temperature for 88 hours (an additional trityl chloride (145.1 mg, 0.52 millimole) being added after 24 hours). The solvent was distilled off from the reaction mixture and the residue was purified over a silicagel column (benzene→ benzene:ethyl acetate=95:5). The product was further repurified over a silicagel column (n-hexane:ether=1:1). The starting compound (12), if present, was recovered from the reaction mixture and treated as described above to give 2-O-pentadecanoyl-3-O-stearoyl-2', 3'-O-(tetraisopropyldisiloxane-1,3-diyl)-6-O-trityl-α,α-trehalose (13) (224 mg, yield 32.6%) in the form of colorless viscous product.

Reference Example ix-5

Preparation of 6'-O-(3-benzyloxy-2n-tetradecyl-docosanoyl)-2-O-pentadecanoyl-3-O-stearoyl-2', 3'-O-(tetraisopropyldisiloxane-1,3-diyl)-6-O-trityl-α,α-trehalose (14)

To a solution of 2-O-pentadecanoyl-3-O-stearoyl-2', 3'-O-(tetraisopropyldisiloxane-1,3-diyl)-6-O-trityl-α,α-trehalose (13) (223.6 mg, 0.17 millimole) dissolved in dry methylene chloride (3 ml,) under argon atmosphere were added 3-benzyloxy-2-n-tetradecyldocosanoic acid (141.8 mg, 0.22 millimole), 4-dimethylaminopyridine (13.5 mg, 0.11 millimole) and N,N'-dicyclohexylcarbodiimide (45.5 mg, 0.22 millimole) successively and the mixture was allowed to react at room temperature for 16 hours. The solvent was distilled off from the reaction mixture and the residue was purified over a silicagel column (benzene) to give 6'-O-(3-benzyloxy-2-n-tetradecyl-docosanoyl)-2-O-pentadecanoyl-3-O-stearoyl-2', 3'-O-(tetraisopropyldisiloxane-1,3-diyl)-6-O-trityl-α,α-trehalose (14) (324.6 mg, yield 98.5%) in the form of colorless viscous product.

Example ix-1

Preparation of 6'-O-(3-hydroxy-2-n-tetradecyl-docosanoyl)-2-O-pentadecanoyl-3-O-stearoyl-α,α-trehalose (Ie-3)

To a solution of 6'-O-(3-benzyloxy-2-n-tetradecyldocosanoyl)-2-O-pentadecanoyl-3-O-stearoyl-2', 3'-O-(tetraisopropyldisiloxane-1,3-diyl)-6-O-trityl-α,α-trehalose (14) (324.6 mg, 0.167 millimole) dissolved in a mixed solvent of dry tetrahydrofuran (8.2 ml), dry acetonitrile (8.2 ml) and water (0.82 ml) was added 1M tetrabutylammonium fluoride in tetrahydrofuran (1.6 ml). The mixture was allowed to react at room temperature for 2 hours and combined with chloroform (about 100 ml). The organic phase was washed with water and dried over anhydrous sodium sulfate. The inorganic salt was filtered off and the solvent was distilled off from the filtrate. The residue was purified over a silicagel column (benzene:ethyl acetate=1:1) to give desilylated product (284.1 mg) in the form of colorless viscous foam.

The desilylated product (284.1 mg) was dissolved in a mixed solvent of dry methylene chloride (3 ml) and dry methanol (3 ml), and the mixture was combined with palladium black (324.6 mg) and hydrogenated at room temperature for 16 hours. The palladium black was filtered off from the reaction mixture and the solvent was distilled off from the filtrate. The residue was purified over a silicagel column (chloroform:methanol=95:5) to give 6'-O-(3-hydroxy-2-n-tetradecyldocosanoyl)-2-O-pentadecanoyl-3-O-stearoyl-α,α-trehalose (Ie-3) (177.5 mg, yield 77.7%) in the form of white solid, m.p. 83°–90° C.

Process x

Reference Example x-1

Preparation of 3,4,3',4'-di-O-(tetraisopropyldisiloxane 1,3-diyl)-α,α-trehalose (15)

A solution of 3,4,3',4'-di-O-(tetraisopropyldisiloxane-1,3-diyl)-6-O-trityl-α,α-trehalose (8) (1.0 g, 0.94 millimole) dissolved in the mixed solvent of dry 1,2-dichloroethane (30 ml) and dry methanol (15 ml) was combined with p-toluenesulfonic acid monohydrate (59 mg, 0.31 millimole). The mixture was allowed to react at room temperature for 1 hour. The solvent was distilled off from the reaction mixture and the residue was purified over a silicagel column (chloroform:methanol=95:5) to give 3,4,3',4'-di-O-(tetraisopropyldisiloxane-1,3-diyl)-α,α-trehalose (15) (360.0 mg, yield 46.5%) in the form of white solid, m.p. 207°–209° C.

IR ($\lambda_{max}$KBr, cm$^{-1}$); 3450, 2940, 2860
$[\alpha]_D^{23}$; +140.82 (C=0.11, CHCl$_3$)
$^1$H-NMR (CDCl$_3$, δ); 0.58-2.41 (m, 56H, -Si-CH=(CH$_3$)$_2$. 3.28-4.28 (m, 16H, glucoside-H). 5.18 (d, 2H, anomer H).

Reference Example x-2

Preparation of 3,4,3',4'-di-O-(tetraisopropyldisiloxane 1,3-diyl)-2,6,6',tri-O-decanoyl-α,α-trehalose (16)

To a solution of 3,4,3,,4'-di-O-(tetraisopropyldisiloxane-1,3-diyl)-α,α-trehalose (15) (216 mg, 0.26 millimole) and n-capric acid (175.8 mg, 1.01 millimole) dissolved in dry methylene chloride (10 ml) were added 4-dimethylaminopyridine (48.1 mg, 0.39 millimole) and N,N'- dicyclohexylcarbodiimide (208.4 mg, 1.01 millimole) successively and the mixture was allowed to react at room temperature for 17 hours. The insoluble matter in the reaction mixture was filtered off by suction and the solvent was distilled off. The residue was purified over a silicagel column (n-hexane:ethyl acetate=9:1) to give 3,4,3',4'-di-O-(tetraisopropyldisiloxane-1,3-diyl)-2,6,6'-tri-O-decanoyl-α,α-trehalose (16) (147 mg, yield 43.8%) in the form of colorless viscous product.

Example x-1

Preparation of 2,6,6'-tri-O-decanoyl-α,α-trehalose (If-1)

A solution of 3,4,3',4'-di-O-(tetraisopropyldisiloxane-1,3-diyl)-2,6,6'-tri-O-decanoyl-α,α-trehalose (16) (147 mg, 0.114 millimole) dissolved in 1M tetrabutylammoniumfluoride/tetrahydrofuran solution (5 ml) was allowed to react at room temperature for 30 minutes. The solvent was distilled off from the reaction mixture and saturated aqueous ammonium chloride solution was added to the residue. The solution was extracted with chloroform. The organic phase was washed with water and dried over anhydrous sodium sulfate. The inorganic salt was filtered off and the solvent was distilled off from the filtrate. The residue was purified over a silicagel column (chloroform:methanol=9:1) to give 2,6,6'-tri-O-decanoyl-α,α-trehalose (If-1) (70.4 mg, yield 76.7%) in the form of colorless viscous product.

The compound (If) in the Table 1, i.e. 2,6,6'-tri-O-pentadecanoyl-α,α-trehalose (If-3) was prepared as described in the above Examples.

Process xi

Reference Example xi-1

Preparation of 6,6'-di-O-(3-O-benzylcorynomycoloyl)-3,4,3',4'-di-O-(tetraisopropyldisiloxane-1,3-diyl)-α,α-trehalose (17)

To a solution of 3,4,3',4'-di-O-(tetraisopropyldisiloxane-1,3-diyl)-α,α-trehalose (15) (200 mg, 0.24 millimole) dissolved in dry methylene choloride (5 ml) were added 3-O-benzylcorynomycolic acid (340.4 mg, 0.58 millimole) in dry methylene chloride (3 ml), 4-dimethylaminopyridine (35.8 mg, 0.29 millimole) and N,N'-dicyclohexylcarbodiimide (119.7 mg, 0.58 millimole) successively and the mixture was allowed to react at room temperature for 16 hours. The insoluble matter in the reaction mixture was filtered off by suction and the solvent was distilled off from the filtrate. The residue was purified over a silicagel column (n-hexane:ethyl acetate=9:1) to give 6,6'-di-O-(3-O-benzylcorynomycoloyl)-3,4,3',4'-di-O-(tetraisopropyldisiloxane)-1,3-diyl)-α,α-trehalose (17) (384 mg in the form of colorless viscous product.

Reference Example xi-2

Preparation of 6,6'-di-O-(3-O-benzylcorynomycoloyl)-3,4,3',4'-di-O-(tetraisopropyldisiloxane-1,3-diyl)-2-O-palmitoyl-α,α-trehalose (16)

To a solution of 6,6'-di-O-(3-O-benzylcorynomycoloyl)-3,4,3',4'-di-O-(tetraisopropyldisiloxane-1,3-diyl)-α,α-trehalose (384 mg) dissolved in dry methylene chloride (8 ml) were added palmitic acid (55.9 mg, 0.218 millimole), 4-dimethylaminopyridine (16.5 mg, 0.134 millimole) and N,N'-dicyclohexylcarbodiimide (45 mg, 0.218 millimole) successively and the mixture was allowed to react at room temperature for 19 hours. The insoluble matter in the reaction mixture was filtered by suction and the solvent was distilled off from the filtrate. The residue was purified over a silicagel column (n-hexane:ethyl acetate=95:5) to give 6,6'-di-O-(3-O-benzylcorynomycoloyl)-3,4,3',4'-di-O-(tetraisopropyldisiloxane-1,3-diyl)-2-O-palmitoyl-α,α-trehalose (16) (110.7 mg) (as a mixture).

Example xi-2

Preparation of 6,6'-di-O-corynomycoloyl-2-O-palmitoyl-α,α-trehalose (If-2)

A solution of 6,6'-di-O-(3-O-benzylcorynomycoloyl)-3,4,3',4'-di-O-(tetraisopropyldisiloxane-1,3-diyl)-2-O-palmitoyl-α,α-trehalose (16) (110.7 mg) (mixture) dissolved in 1M tetrabutylammoniumfluoride/tetrahydrofuran solution (4 ml) was allowed to react at room temperature for 30 minutes. The solvent was distilled off from the reaction mixture and saturated aqueous saturated ammonium chloride solution was added to the residue. The mixture was extracted with chloroform. The organic phase was washed with water and dried over anhydrous sodium sulfate. The inorganic salt was filtered off and the solvent was distilled off from the filtrate. The residue was purified over a silicagel column (chloroform:methanol=95:5) to give desilylated product in the form of colorless viscous product.

The desilylated product was dissolved in a mixed solvent of dry methanol (1.5 ml) and dry methylene chloride (1.5 ml) Palladium black (140 mg) was added and the mixture was hydrogenated at room temperature for 19 hours. The palladium black was filtered off from the reaction mixture and the solvent was distilled off from the filtrate. The residue was purified over a silicagel column (chloroform:methanol=9:1) to give 6,6'-di-O-corynomycoloyl-2-O-palmitoyl-α,α-trehalose (If-2) (60 mg, yield 16.3% based on the compound (15)) in the form of colorless viscous product.

The compound (If) in the Table 1, i.e. 2,6,6'-tri-O-corynomycoloyl-α,α-trehalose (If-4) was prepared as described in the above Examples.

Example xii-1

Preparation of 2,3,6,6'-tetra-O-oleoyl-α,α-trehalose (Ig-1)

To a solution of 2,3-di-O-oleoyl-2', 3'-O-(tetra-isopropyldisiloxane-1,3-diyl)-α,α-trehalose (12) (570 mg, 0.512 millimole) dissolved in dry methylene chloride (12 ml) were added oleic acid (0.394 ml, 1.23 millimole), 4-dimethylaminopyridine(75 mg, 0.614 millimole) and N,N'-dicyclohexylcarbodiimide (254 mg, 1.23 millimole) successively and the mixture was allowed to react at room temperature for 4 hours. The precipitates formed in the reaction mixture were filtered off by suction and the solvent was distilled off from the filtrate. The residue was dissolved in a developing solvent (benzene:ethyl acetate=98:2) and purified over a silicagel column (benzene:ethyl acetate=98:2). The fast eluting solution comprising impurities were discarded and colorless fractions were pooled. The solvent was distilled off to give 2', 3'-O-(tetraisopropyldisiloxane-1,3-diyl)-2,3,6,6'-tetra-O-oleoyl-α,α-trehalose (18) (501.7 mg) (as a mixture) in the form of colorless viscous product. The obtained mixture (501.7 mg) was dissolved in a mixed solvent of dry tetrahydrofuran (10 ml), dry acetonitrile (10 ml) and water (1 ml), and 1M tetrabutylammonium fluoride in tetrahydrofuran (3.05 ml) was added thereto. The mixture was allowed to react at room temperature for 1 hour, combined with chloroform (about 100 ml) and washed with saturated aqueous ammonium chloride solution and water, then dried over anhydrous sodium sulfate. The inorganic salt was filtered off and the solvent was distilled off from the filtrate. The residue was dissolved in a developing solvent (chloroform:methanol=95:5) and fractionated through a silicagel column (chloroform:methanol=95:5). The fast eluting solution comprising impurities were discarded and colorless fractions were pooled. The solvent was distilled off therefrom to give 2,3,6,6'-tetra-O-oleoyl-$\alpha,\alpha$-trehalose (Ig-1) (288.8 mg, yield 28.7%) in the form of colorless viscous product.

Example xii-2

Preparation of 6,6'-di-O-(3-hydroxy-2-n-tetradecyl-docosanoyl)-2,3-di-O-pentadecanoyl-$\alpha,\alpha$-trehalose (Ig-2)

To a solution of 2,3-di-O-pentadecanoyl-2', 3'-O-(tetraisopropyldisiloxane-1,3-diyl)-$\alpha,\alpha$-trehalose (12) (692.5 mg, 0.67 millimole) dissolved in dry methylene choloride (12 ml) were added 3-benzyloxy-2-n-tetradecyl-docosanoic acid (1.033 g, 1.61 millimole) in dry methylene chloride (3 ml), 4-dimethylaminopyridine (97.7 mg, 0.8 millimole) and N,N'-dicyclohexylcarbodiimide (332.2 mg, 1.61 millimole) successively and the mixture was allowed to react at room temperature for 20 hours. The precipitates formed in the reaction mixture were filtered by suction and the solvent was distilled off from the filtrate. The residue was dissolved in a developing solvent (benzene) and fractionated through a silicagel column (benzene). The fast eluting solution comprising impurities were discarded and colorless fractions were pooled. The solvent was distilled off to give 6,6'-di-O-(3-benzyloxy-2-n-tetradecyldocosanoyl)-2,3-di-O-pentadecanoyl-2', 3'-O-(tetraisopropyldisiloxane-1,3-diyl-$\alpha,\alpha$-trehalose (18) (747.5 mg) in the form of colorless viscous product. The compound (18) was dissloved in a mixed solvent of dry tetrahydrofuran (5 ml), dry acetonitrile (5 ml) and water (0.2 ml), and 1M tetrabutylammonium fluoride in tetrahydrofuran (3.3 ml) was added thereto. The mixture was allowed to react at room temperature for 1 hour and combined with chloroform (100 ml). The mixture was washed with saturated aqueous ammonium chloride solution and water, and then dried over anhydrous sodium sulfate. The inorganic salt was filtered off and the solvent was distilled off from the filtrate. The residue was dissolved in a developing solvent (benzene:ethyl acetate=65:35) and fractionated through a silicagel column (benzene:ethyl acetate=65:35). The fast eluting solution comprising impurities were discarded and colorless fractions were pooled. The solvent was distilled off therefrom to give desilylated product, 6,6'-di-O-(3-benzyloxy-2-n-tetradecyldocosanoyl)-2,3-di-O-pentadecanoyl-$\alpha,\alpha$-trehalose (388.1 mg) in the form of colorless viscous foam. The desilylated product (388.1 mg) was dissolved in a mixed solvent of dry methylene chloride (4 ml) and dry ethanol (4 ml). The mixture was combined with palladium black (388.1 mg) and hydrogenated at room temperature for 14 hours. The palladium black was filtered off from the reaction mixture and the solvent was filtered off from the filtrate. The residue was dissolved in a developing solvent (chloroform:methanol=95:5) and fractionated through a silicagel column (chloroform:methanol=95:5). The fast eluting fractions comprising impurities were discarded and colorless fractions were pooled. The solvent was distilled off to give 6,6'-di-O-(3-hydroxy-2-n-tetradecyldocosanoyl)-2 3-di-O-pentadecanoyl-$\alpha,\alpha$-trehalose (Ig-2) (297.8 mg, yield 16.1%) in the form of white viscous foam. The compound (Ig) in the Table 1, i.e. 6,6'-di-O-oleoyl-2,3-di-O-pentadecanoyl-$\alpha,\alpha$-trehalose (Ig-3) and 2,3-di-O-oleoyl-6,6'-di-O-pentadecanoyl-$\alpha,\alpha$-trehalose (Ig-4) were prepared as described in the above Examples.

The physicochemical properties of the compounds of the present invention prepared according to the above Reference Examples and Examples are summarized in Table 1.

TABLE 1

| Compound No. | A | B | C | D | Appearance |
|---|---|---|---|---|---|
| Ic-1 | —OC(=O)—(CH$_2$)$_4$CH$_3$ | —OH | —OH | —OC(=O)—(CH$_2$)$_4$CH$_3$ | colorless viscous product |
| Ic-2 | —OC(=O)—(CH$_2$)$_8$CH$_3$ | —OH | —OH | —OC(=O)—(CH$_2$)$_8$CH$_3$ | white crystals |
| Ic-3 | —OC(=O)—(CH$_2$)$_{13}$CH$_3$ | —OH | —OH | —OC(=O)—(CH$_2$)$_{13}$CH$_3$ | white foamy product |
| Ic-4 | —OC(=O)—(CH$_2$)$_{18}$CH$_3$ | —OH | —OH | —OC(=O)—(CH$_2$)$_{18}$CH$_3$ | white crystals |
| Ic-5 | —OC(=O)—(CH$_2$)$_7$CH=CH—(CH$_2$)$_7$CH$_3$ | —OH | —OH | —OC(=O)—(CH$_2$)$_7$CH=CH—(CH$_2$)$_7$CH$_3$ | colorless viscous product |
| Ic-6 | —OC(=O)—(CH$_2$)$_7$CH=CHCH$_2$CH=CH(CH$_2$)$_4$CH$_3$ | —OH | —OH | —OC(=O)—(CH$_2$)$_7$CH=CHCH$_2$CH=CH(CH$_2$)$_4$CH$_3$ | white waxy product |
| Ic-7 | —OC(=O)—(CH$_2$)$_7$CH(—O—)CH(CH$_2$)$_7$CH$_3$ | —OH | —OH | —OC(=O)—(CH$_2$)$_7$CH(—O—)CH(CH$_2$)$_7$CH$_3$ | colorless viscous product |
| Ic-7 | —OC(=O)—CH—CH(OH)—(CH$_2$)$_4$CH$_3$ ((CH$_2$)$_{13}$CH$_3$) | —OH | —OH | —OC(=O)—CH—CH(OH)—(CH$_2$)$_4$CH$_3$ ((CH$_2$)$_{13}$CH$_3$) | colorless viscous product |
| Ic-8 | —OC(=O)—(CH$_2$)$_{13}$CH$_3$ | —OH | —OH | —OC(=O)—(CH$_2$)$_{13}$CH$_3$ | colorless viscous product |

TABLE 1-continued

化合物 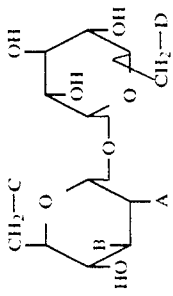

| 化合物 | B | A | C | D | |
|---|---|---|---|---|---|
| Ic-9 | —OC—(CH$_2$)$_{13}$CH$_3$ (O=) | —OH | —OH | —OC—CH—(CH$_2$)$_{14}$CH$_3$ (O=, OH, (CH$_2$)$_{13}$CH$_3$) | white foamy crystals |
| Ic-10 | —OC—(CH$_2$)$_{13}$CH$_3$ (O=) | —OH | —OH | —OC—CH—(CH$_2$)$_{18}$CH$_3$ (O=, OH, (CH$_2$)$_{13}$CH$_3$) | white waxy product |
| Ic-11 | —OC—(CH$_2$)$_7$CH=CHCH$_2$CH=CH(CH$_2$)$_4$CH$_3$ (O=) | —OH | —OH | —O—C—(CH$_2$)$_7$CH=CH(CH$_2$)$_7$CH$_3$ (O=) | white foamy viscous product |
| Ic-12 | —O—C—(CH$_2$)$_{13}$CH$_3$ (O=) | —OH | —OH | —O—C—(CH$_2$)$_{14}$CH$_3$ (O=) | white foamy viscous product |
| Ic-13 | —O—C—(CH$_2$)$_{13}$CH$_3$ (O=) | —OH | —OH | —O—C—CH—CH(CH$_2$)$_7$CH=CH(CH$_2$)$_7$CH$_3$ (O=, OH, (CH$_2$)$_{13}$CH$_3$) | colorless waxy product |
| Ic-14 | —O—C—(CH$_2$)$_7$CH=CH(CH$_2$)$_7$CH$_3$ (O=) | —OH | —OH | —O—C—CH—CH(CH$_2$)$_7$CH=CH(CH$_2$)$_7$CH$_3$ (O=, OH, (CH$_2$)$_{13}$CH$_3$) | white waxy product |
| Ic-15 | —O—C—(CH$_2$)$_7$CH=CH(CH$_2$)$_7$CH$_3$ (O=) | —OH | —OH | —O—C— (retinoyl group) | yellow foamy viscous product |
| Ia-1 | —OC—(CH$_2$)$_7$CH=CH(CH$_2$)$_7$CH$_3$ (O=) | —OH | —OH | —OH | white viscous solid |

TABLE 1-continued

| 化合物 | A | B | C | D | Appearance |
|---|---|---|---|---|---|
| Ia-2 | $-OC(=O)-CHCH(CH_2)_{14}CH_3$ with $OH$ on CH and $(CH_2)_{13}CH_3$ branch | $-OH$ | $-OH$ | $-OH$ | white solid |
| Ia-3 | $-OC(=O)-(CH_2)_{13}CH_3$ | $-OH$ | $-OH$ | $-OH$ | white waxy solid |
| Ia-4 | $-OC(=O)-(CH_2)_{10}CH(OH)(CH_2)_5CH_3$ | $-OH$ | $-OH$ | $-OH$ | white solid |
| Ia-5 | $-OC(=O)-(CH_2)_7CH=CHCH_2CH=CH(CH_2)_4CH_3$ | $-OH$ | $-OH$ | $-OH$ | white foamy viscous solid |
| Iac-1 | $-OC(=O)-(CH_2)_7CH\underset{\diagdown O \diagup}{-}CH(CH_2)_7CH_3$ (epoxide) | $-OH$ | $-OH$ | $-OH$ | white foamy viscous solid |
| Ib-1 | $-OH$ | $-OC(=O)-CHCH(CH_2)_{14}CH_3$ with $OH$ and $(CH_2)_{13}CH_3$ branch | $-OH$ | $-OH$ | white waxy solid |
| Ib-2 | $-OH$ | $-OC(=O)-(CH_2)_{14}CH_3$ | $-OH$ | $-OH$ | white solid |
| Ib-3 | $-OH$ | $-OC(=O)-CHCH(CH_2)_{18}CH_3$ with $OH$ and $(CH_2)_{13}CH_3$ branch | $-OH$ | $-OH$ | colorless viscous solid |
| Id-1 | $-OC(=O)-(CH_2)_7CH=CH(CH_2)_7CH_3$ | $-OC(=O)-(CH_2)_7CH=CH(CH_2)_7CH_3$ | $-OH$ | $-OH$ | white foamy viscous product |

TABLE 1-continued

| 化合物 | B | A | C | D | |
|---|---|---|---|---|---|
| Id-2 | $-OC(=O)-(CH_2)_7CH=CH(CH_2)_7CH_3$ | $-OC(=O)-(CH_2)_7CH=CHCH_2CH=CH(CH_2)_4CH_3$ | $-OH$ | $-OH$ | colorless glassy solid |
| Id-3 | $-OC(=O)-CH(OH)CH(CH_2)_{13}CH_3$<br>$(CH_2)_{13}CH_3$ | $-OC(=O)-CHCH(CH_2)_4CH_3$<br>$OH$ $(CH_2)_{13}CH_3$ | $-OH$ | $-OH$ | white waxy solid |
| Id-4 | $-OC(=O)-(CH_2)_{13}CH_3$ | $-OC(=O)-(CH_2)_{16}CH_3$ | $-OH$ | $-OH$ | white solid |
| Id-5 | $-OC(=O)-(CH_2)_{13}CH_3$ | $-OC(=O)-(CH_2)_{13}CH_3$ | $-OH$ | $-OH$ | white solid |
| Id-6 | $-OC(=O)-(CH_2)_{13}CH_3$ | $-OC(=O)-(CH_2)_7CH=CH(CH_2)_7CH_3$ | $-OH$ | $-OH$ | white foamy solid |
| Id-7 | $-OC(=O)-(CH_2)_{13}CH_3$ | $-OC(=O)-CHCH(CH_2)_4CH_3$<br>$OH$ $(CH_2)_{13}CH_3$ | $-OH$ | $-OH$ | colorless waxy solid |
| Id-8 | $-OC(=O)-(CH_2)_{10}CH(CH_2)_5CH_3$<br>$OH$ | $-OC(=O)-(CH_2)_{13}CH_3$ | $-OH$ | $-OH$ | colorless waxy solid |
| Id-9 | $-OC(=O)-(CH_2)_{10}CH(CH_2)_5CH_3$<br>$OH$ | $-OC(=O)-(CH_2)_{10}CH(CH_2)_5CH_3$<br>$OH$ | $-OH$ | $-OH$ | white foamy solid |
| Id-10 | $-OC(=O)-(CH_2)_{10}CH(CH_2)_5CH_3$<br>$OH$ | $-OC(=O)-(CH_2)_7CH-CH(CH_2)_7CH_3$<br>$\diagdown CH_2\diagup$ | $-OH$ | $-OH$ | white foamy solid |
| Id-11 | $-OC(=O)-(CH_2)_{10}CH(CH_2)_5CH_3$<br>$OH$ | $-OC(=O)-(CH_2)_7CH=CH(CH_2)_7CH_3$ | $-OH$ | | white waxy solid |

TABLE 1-continued

化合物

Structure header: CH₂—C / O / B / HO / A, linked to another ring with OH, OH, O, CH₂—D

| Compound | A | B | C | D | Appearance |
|---|---|---|---|---|---|
| 1d-12 | $-OC(=O)-(CH_2)_7CH=CHCH_2CH=CH(CH_2)_4CH_3$ | $-OC(=O)-(CH_2)_7CH=CHCH_2CH=CH(CH_2)_4CH_3$ | —OH | —OH | colorless oil |
| 1dc-1 | $-OC(=O)-(CH_2)_7CH\underset{O}{-}CH(CH_2)_7CH_3$ (epoxide) | $-OC(=O)-(CH_2)_7CH\underset{O}{-}CH(CH_2)_7CH_3$ (epoxide) | —OH | —OH | white waxy solid |
| 1e-1 | $-OC(=O)-(CH_2)_7CH=CH(CH_2)_7CH_3$ | $-OC(=O)-(CH_2)_7CH=CH(CH_2)_7CH_3$ | —OH | $-OC(=O)-(CH_2)_7CH\underset{\underset{CH_2}{|}}{-}CH-CH(CH_2)_7CH_3$ | white foamy viscous solid |
| 1e-2 | $-OC(=O)-(CH_2)_7CH=CH(CH_2)_7CH_3$ | $-OC(=O)-(CH_2)_7CH=CH(CH_2)_7CH_3$ | —OH | $-OC(=O)-CHCH(CH_2)-CH=CH(CH_2)_7CH_3$ with OH and $(CH_2)_{13}CH_3$ | white waxy solid |
| 1e-3 | $-OC(=O)-(CH_2)_{16}CH_3$ | $-OC(=O)-(CH_2)_{16}CH_3$ | —OH | $-OC(=O)-CHCH(CH_2)_{18}CH_3$ with OH and $(CH_2)_{13}CH_3$ | white solid |
| 1e-4 | $-OC(=O)-(CH_2)_{13}CH_3$ | $-OC(=O)-(CH_2)_{13}CH_3$ | —OH | $-OC(=O)-(CH_2)_{13}CH_3$ | colorless waxy solid |
| 1e-5 | $-OC(=O)-(CH_2)_7CH=CHCH_2CH=CH(CH_2)_4CH_3$ | $-OC(=O)-(CH_2)_7CH=CHCH_2CH=CH(CH_2)_4CH_3$ | —OH | $-OC(=O)-(CH_2)_7CH=CH(CH_2)_7CH_3$ | colorless viscous product |
| 1e-6 | $-OC(=O)-(CH_2)_{13}CH_3$ | $-OC(=O)-(CH_2)_{13}CH_3$ | —OH | $-OC(=O)-(CH_2)_7CH=CH(CH_2)_7CH_3$ | colorless foamy viscous product |
| 1e-7 | $-OC(=O)-(CH_2)_7CH=CH(CH_2)_7CH_3$ | $-OC(=O)-(CH_2)_7CH=CH(CH_2)_7CH_3$ | —OH | $-OC(=O)-(CH_2)_{13}CH_3$ | white foamy viscous product |

TABLE 1-continued

化合物 structure:
$$\text{CH}_2\text{—C} \quad \text{OH}$$
with rings A, B and $\text{CH}_2\text{—D}$, bearing OH groups

| Compound | A | B | C | D |
|---|---|---|---|---|
| If-1 | —OC(=O)—(CH$_2$)$_8$CH$_3$ | —OH | —OC(=O)—(CH$_2$)$_8$CH$_3$ | colorless viscous product |
| If-2 | —OC(=O)—(CH$_2$)$_{14}$CH$_3$ | —OH | —OC(=O)—CH(OH)CH(CH$_2$)$_{14}$CH$_3$ $\vert$ (CH$_2$)$_{13}$CH$_3$ | colorless viscous product |
| If-3 | —OC(=O)—(CH$_2$)$_{13}$CH$_3$ | —OH | —OC(=O)—(CH$_2$)$_{13}$CH$_3$ | colorless viscous product |
| If-4 | —OC(=O)—CH(OH)CH(CH$_2$)$_{14}$CH$_3$ $\vert$ (CH$_2$)$_{13}$CH$_3$ | —OH | —OC(=O)—CH(OH)CH(CH$_2$)$_{14}$CH$_3$ $\vert$ (CH$_2$)$_{13}$CH$_3$ | colorless viscous product |
| Ig-1 | —OC(=O)—(CH$_2$)$_7$CH=CH(CH$_2$)$_7$CH$_3$ | —OC(=O)—(CH$_2$)$_7$CH=CH(CH$_2$)$_7$CH$_3$ | —OC(=O)—(CH$_2$)$_7$CH=CH(CH$_2$)$_7$CH$_3$ | colorless viscous product |
| Ig-2 | —OC(=O)—(CH$_2$)$_{13}$CH$_3$ | —OC(=O)—(CH$_2$)$_{13}$CH$_3$ | —OC(=O)—CH(OH)CH(CH$_2$)$_{18}$CH$_3$ $\vert$ (CH$_2$)$_{13}$CH$_3$ | white foamy viscous product |
| Ig-3 | —OC(=O)—CH(OH)CH(CH$_2$)$_{14}$CH$_3$ $\vert$ (CH$_2$)$_{13}$CH$_3$ | —OC(=O)—(CH$_2$)$_{13}$CH$_3$ | —OC(=O)—CH(OH)CH(CH$_2$)$_{14}$CH$_3$ $\vert$ (CH$_2$)$_{13}$CH$_3$ | colorless viscous product |
| Ig-4 | —OC(=O)—(CH$_2$)$_7$CH=CH(CH$_2$)$_7$CH$_3$ | —OC(=O)—(CH$_2$)$_7$CH=CH(CH$_2$)$_7$CH$_3$ | —OC(=O)—(CH$_2$)$_{13}$CH$_3$ | colorless viscous product |

| Compound No. | Yield (%)* | Optical rotation(°) [α]$_D^{23}$ (Chloroform) | IR (cm$^{-1}$) | $^1$H—NMR (CDCl$_3$, δ) | FAB—MS (m/z)(M + Na$^+$) |
|---|---|---|---|---|---|
| Ic-1 | 33 | +105.68° (c = 0.105) | 3350, 2950 1730 | 0.53~5.70(m, 42H) | 561 |
| Ic-2 | 17 | +110.28° (c = 0.105) | 3300, 2950 1730 | 0.57~2.70(m, 38H) 2.77~5.47(m, 20H) | 674 |

TABLE 1-continued

化合物

[Structure: CH₂—C / O / B / HO, connected to A, linked via O to another ring with OH, OH, CH₂—D]

| Compound No. | Optical rotation [α]_D (°) | Rf volume (Chloroform:Methanol) | M.P. (°C.) | Yield (%)* | IR(cm⁻¹) (film or KBr) | ¹H-NMR | FAB — MS (m/z) |
|---|---|---|---|---|---|---|---|
| Ic-3 | +86.81° (c = 0.107) | | | 25 | 3400, 2950 1730 | 0.33~2.60(m, 58H) 2.77~5.33(m, 20H) | 814 |
| Ic-4 | +95.30° (c = 0.109) | | | 11 | 3400, 2910 1740 | not measured | 954 |
| Ic-5 | +68.85° (c = 0.102) | | | 14 | 3400, 2950 1730 | 0.53~5.43(m, 86H) | 894 |
| Ic-6 | +62.37° (c = 0.105) | | | 24 | 3300, 2900 1720 | 0.48~5.80(m, 82H) | 890 |
| Ic-1 | +73.41° (c = 0.11) | | | 8 | 3400, 2950 1730 | 0.47~5.30(m, 86H) | 926 |
| Ic-7 | +54.58° (c = 0.1) | | | 8 | 3400, 2950 1730 | 0.59~1.59(m, 120H) 2.03~5.59(m, 26H) | 1323 |
| Ic-8 | +80.13° (c = 0.107) | | | 10 | 3400, 2900 1730 | 0.48~5.62(m, 82H) | 853 |
| Ic-9 | +60.03° (c = 0.107) | | | 28 | 3400, 2900 1730 | 0.40~5.57(m, 112H) | 1067 |
| Ic-10 | +53.84° (c = 0.058) | | | 5 | 3400, 2950 1730 | 0.40~5.57(m, 120H) | 1124 |
| Ic-11 | +82.16° (c = 0.1) | | | 15.2 | 3350, 2900 1730 | 0.67~5.87(m, 84H) | 891 |
| Ic-12 | +88.60° (c = 0.128) | | | 15.1 | 3400, 2900 1740 | 0.57~5.67(m, 80H) | 827 |
| Ic-13 | +64.23° (c = 0.470) | | | 17.0 | 3400, 2920 1740 | 5.0~5.43(m, 2H, CH=CH) 0.60~4.37(m, 112H) | 1094 |
| Ic-14 | +61.28° (c = 0.33) | | | 6.4 | 3400, 2920 1740 | 5.0~5.60(m, 4H, —CH=CH—) 0.50~5.0(m, 114H) | 1134 |
| Ic-15 | not measured (insoluble in CHCl₃) | | | 17.1 | 3350, 2910, 2850 1740, 1710 | not measured | 912 |

TABLE 1-continued

![structure: CH2—C / O / B / HO / A / O / OH / OH / CH2—D]

| 化合物 | [α] | Rf | mp (°C) | structure val | IR | MS |
|---|---|---|---|---|---|---|
| Ia-1 | +118.32 (c = 0.120,EtOH) (t 22) | 0.22 (8:2) | 90–100 | 48.9 | 3350, 2930 1730 | 737 (M + Na + thioglycerol)+ |
| Ia-2 | +101.20 (c = 0.243,CHCl3) (t 21) | 0.39 (8:2) | 95–105 | 4.6 | 3350, 2900 2850, 1730 | 843 (M + Na)+ |
| Ia-3 | +134.53 (c = 0.35,EtOH) (t 24) | 0.34 (7:3) | 155–160 | 35.9 | 3400, 1730 | 589 (M + Na)+ |
| Ia-4 | +100.72 (c = 0.214,EtOH) (t 25) | 0.32 (7:3) | 70–80 | 21.9 | 3350, 2920 1730 | 647 (M + Na)+ |
| Ia-5 | +110.91 (c = 0.294,EtOH) (t 22) | 0.33 (7:3) | 70–75 | 47.2 | 3380, 2920 1730 | 735 (M + Na + thioglycerol)+ |
| Iac-1 | +106.09 (c = 0.424,EtOH) (t 22) | 0.22 (8:2) | 55–65 | 33.9 | 3350, 2920 1730 | 645 (M + Na)+ |
| Ib-1 | +87.63 (c = 0.398,CHCl3) (t 20) | 0.39 (8:2) | 203–209 | 14.6 | 3400, 1720 | 844 (M + Na)+ |
| Ib-2 | +138.19 (c = 0.309,EtOH) (t 20) | 0.39 (7:3) | 109–121 | 19.0 | 3400, 2920 2850, 1730 | 603 (M + Na)+ |
| Ib-3 | +84.63 (c = 0.484,CHCl3) (t 23) | 0.32 (8:2) | — | 32.9 | 3400, 2910 2850, 1720 | 899 (M + Na)+ |
| Id-1 | +82.77 (c = 0.293,CHCl3) (t 23) | 0.48 (8:2) | 102–113 | 63.6 | 3350, 2910 1735 | 893 (M + Na)+ |
| Id-2 | +88.60 (c = 0.697,CHCl3) (t 21) | 0.21 (85:15) | 85–114 | 50.3 | 3400, 2920 1740 | 891 (M + Na)+ |
| Id-3 | +142.41 (c = 0.112,CHCl3) (t 23) | 0.50 (85:15) | 159–163 | 8.5 | 3400, 1730 | 1322 |
| Id-4 | +90.66 (c = 0.20,EtOH) (t 22) | 0.35 (8:2) | 123–127 | 41.5 | 3350, 2920 1740 | 855 (M + Na)+ |
| Id-5 | +93.77 (c = 0.270,EtOH) (t 21) | 0.29 (8:2) | 133 | 59.5 | 3370, 2920 1740 | 813 (M + Na)+ |

| 化合物 | | | | | |
|---|---|---|---|---|---|
| Id-6 | +86.66(t 23)<br>(c = 0.234,CHCl₃) | 0.32<br>(8:2) | 118–120 | 44.4 | 3360, 2920 1735 | 853<br>(M + Na)⁺ |
| Id-7 | +66.07(t 25)<br>(c = 0.506,CHCl₃) | 0.38<br>(85:15) | 189–190 | 8.6 | 3380, 2920 1735 | 1068<br>(M + Na)⁺ |
| Id-8 | +87.63(t 23)<br>(c = 0.422,CHCl₃) | 0.30<br>(85:15) | 82–92 | 20.8 | 3400, 2920 1740 | 871<br>(M + Na)⁺ |
| Id-9 | +83.39(t 21)<br>(c = 0.311,CHCl₃) | 0.34<br>(8:2) | 101–111 | 21.9 | 3370, 2920 1740 | 929<br>(M + Na)⁺ |
| Id-10 | +76.65(t 22)<br>(c = 0.348,CHCl₃) | 0.19<br>(85:15) | 55–65 | 23.4 | 3350, 2920 1740 | 925<br>(M + Na)⁺ |
| Id-11 | +79.10(t 23)<br>(c = 0.529,CHCl₃) | 0.18<br>(85:15) | 51–60 | 24.5 | 3350, 2920 1740 | 911<br>(M + Na)⁺ |
| Id-12 | +59.59(t 23)<br>(c = 1.062,CHCl₃) | 0.19<br>(9:1) | — | 26.1 | 3350, 2910 1735 | 889<br>(M + Na)⁺ |
| Ide-1 | +77.80(t 22)<br>(c = 0.438,CHCl₃) | 0.34<br>(85:15) | — | 39.0 | 3350, 2910 1730 | 925<br>(M + Na)⁺ |
| Ie-1 | +59.35(t 24)<br>(c = 0.268,CHCl₃) | 0.50<br>(9:1) | — | 12.6 | 3300, 2900 1730 | 1171<br>(M + Na)⁺ |
| Ie-2 | +48.52(t 21)<br>(c = 0.244,CHCl₃) | 0.33<br>(9:1) | 85–90 | 6.3 | 3400, 2940 1740 | 1398<br>(M + Na)⁺ |
| Ie-3 | +50.19(t 21)<br>(c = 0.497,CHCl₃) | 0.29<br>(95:5) | 83–90 | 14.8 | 3400, 2920 1740 | 1390<br>(M + Na)⁺ |
| Ie-4 | +58.98(t 24)<br>(c = 0.863,CHCl₃) | 0.30<br>(9:1) | 47–49 | 14.6 | 3400, 2920 1740 | 1038<br>(M + Na)⁺ |
| Ie-5 | +54.92(t 23)<br>(c = 0.541,CHCl₃) | 0.47<br>(9:1) | — | 9.4 | 3400, 2910 2850, 1740 | 1151<br>(M + Na)⁺ |
| Ie-6 | +60.57(t 23)<br>(c = 0.296,CHCl₃) | 0.31<br>(9:1) | — | 7.6 | 3450, 2920 1740 | 1077<br>(M + Na)⁺ |

TABLE 1-continued

| 化合物 | | | [structure: CH₂-C / B / HO / O / A / OH / OH / CH₂-D] | | |
|---|---|---|---|---|---|
| Ie-7 | +63.96(t = 23)<br>(c = 0.268,CHCl₃) | 0.54<br>(9:1) | 11.5 | 3350, 2920 1740 | 1117<br>(M + Na)⁺ |
| If-1 | +58.27(t = 23)<br>(c = 0.115,CHCl₃) | 0.28<br>(9:1) | 33.6 | 3400, 2900 1730 | 828<br>(M + Na)⁺ |
| If-2 | +20.29(t = 23)<br>(c = 0.108,CHCl₃) | 0.49<br>(9:1) | 16.3 | 3350, 2900 1730 | 1561<br>(M + Na)⁺ |
| If-3 | +56.31(t = 23)<br>(c = 0.116,CHCl₃) | 0.22<br>(9:1) | 22.2 | 3350, 2900 1730 | 1038<br>(M + Na)⁺ |
| If-4 | +43.71(t = 23)<br>(c = 0.053,CHCl₃) | 0.28<br>(95:5) | 2.4 | 3350, 2900 1730 | 1801<br>(M + Na)⁺ |
| Ig-1 | +42.96(t = 24)<br>(c = 2.888,CHCl₃) | 0.22<br>(95:5) | 28.9 | 3410, 2910 1740 | 1423<br>(M + Na)⁺ |
| Ig-2 | +37.10(t = 23)<br>(c = 2.952,CHCl₃) | 0.18<br>(95:5) | 16.1 | 3400, 2900 2850, 1730 | 1883<br>(M + Na)⁺ |
| Ig-3 | +29.57(t = 23)<br>(c = 1.887,CHCl₃) | 0.33<br>(95:5) | 21.2 | 3450, 2920 2850, 1740 | 1342<br>(M + Na)⁺ |
| Ig-4 | +45.00(t = 24)<br>(c = 4.215,CHCl₃) | 0.31<br>(95:5) | 46.9 | 3400, 2900 1740 | 1342<br>(M + Na)⁺ |

*Yields are based on the compound (8) for Ic-1 – 15 and Iee-1.
Yields are based on the compound (3) for Ia-1,3 – 5, Iac-1, Ib-1 – 3, Id-1 – 12, Idc-1, Ie-1 – 7, Ig-1 – 4
Yields are based on the compound (1) for Ia-2
Yields are based on the compound (15) for If-1 – 4
■ yield based on the α,α-trehalose starting material

What is claimed is:
1. A trehalose derivative of the formula;

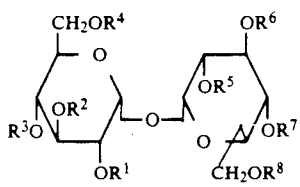

wherein one, two, three of four of $R^1$, $R^2$, $R^3$, $R^4$, $R^5$, $R^6$, $R^7$, and $R^8$ are independently selected from the group consisting of unsubstituted or substituted $C_{1-40}$ aliphatic acyl groups and all the rest of them are hydrogen atoms wherein the substituted aliphatic group contains at least one substituent selected from the group consisting of hydroxy, methoxy, epoxy, oxo, carboxy, protected carboxy, methylene, 2, 6, 6-tremethyl-1-cyclehexen-b 1-yl, alkylcycloalkyl, cycloalkenyl, protected hdyroxy wherein the hydoxy protected group is selected from the group consisting of α-aryl (lower) alkyl,trifluoro-, chloro-, methoxy- or aryloxy-acetyl, (lower) alkoxy carbonyl, 2-tetrahydropyranyl, 2-tetrahydrothiopyranyl, tri (lower alkylsilyl, tri (lower) alkylmethyl, 1-(α-aryl (lower) alkyloxycarbonyl amino)-2, 2, 2-trifluoroethyl, 2-(α-aryl (lower) alkyloxy carbonyl) benzoyl, tri (lower) alkylmethyloxy carbonyl, arylcarbonyl(lower)alkylcarbonyl, lower alkylidene which may be substituted with monocyclic aryl, lower alkoxy and oxo and polysiloxanediyl with the proviso that:
 a) when one of them is $C_{1-40}$ aliphatic acyl group, then it is not 2-palmitoyl or 6-aliphatic acyl,
 (b when two of them are $C_{1-40}$ aliphatic acyl group, then they are not located at corresponding positions with each other,
 c) when three of them are $C_{1-40}$ aliphatic acyl groups, then they are not 2,3,2'-tripalmitoyl, and
 d) when four of them ar $C_{1-40}$ aliphatic acyl groups, then they are not located at corresponding positions with each other or at 2,3,4,2'- or 2,3,6,2'-positions.

2. The trehalose derivative according to claim 1 which is represented by the formula:

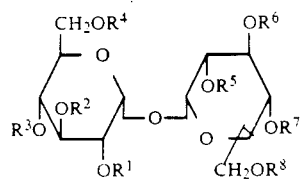

wherein one of $R^1$, $R^2$, $R^3$, $R^4$, $R^5$, $R^6$, $R^7$, and $R^8$ is independently selected from the group consisting of $C_{1-40}$ aliphatic acyl groups other than 2-palmitoyl or 6-aliphatic acyl and all the rest of them are hydrogen atoms.

3. The trehalose derivative according to claim 2 wherein said one group is located at the 2- or 3-position.

4. The trehalose derivative according to claim 2 wherein said one groups is straight or branched, saturated or unsaturated $C_6$–$C_{36}$ aliphatic acyl group.

5. The trehalose derivative according to claim 4 wherein said one group is substituted with hydroxy or epoxy.

6. The trehalose derivative according to claim 1 which is represented by the formula:

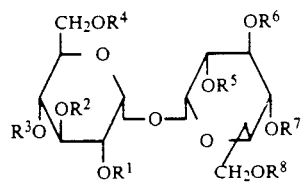

wherein two of $R^1$, $R^2$, $R^3$, $R^4$, $R^5$, $R^6$, $R^7$, and $R^8$ are independently selected from the group consisting of unsubstituted or substituted $C_{1-40}$ aliphatic acyl groups and all the rest of them are hydrogen atoms, with the proviso that said two are not located at corresponding positions with each other.

7. The trehalose derivative according to claim 6 wherein said two groups are located at 2,3- or 2,6'-positions.

8. The trehalose derivative according to claim 6 wherein said two groups are straight or branched, saturated or unsaturated $C_6$–$C_{36}$ aliphatic acyl group.

9. The trehalose derivative according to claim 6 wherein at least one group of said two groups is substituted with hydroxy, epoxy, alkylcycloalkyl or cycloalkenyl.

10. The trehalose derivative according to claim 1 which is represented by the formula:

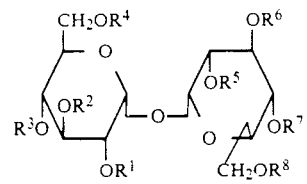

wherein three of $R^1$, $R^2$, $R^3$, $R^4$, $R^5$, $R^6$, $R^7$, and $R^8$ are independently selected from consisting of unsubstituted or substituted $C_{1-40}$ aliphatic acyl groups and all the rest of them are hydrogen atoms, with the proviso that said three are not 2,3,2'-tripalmitoyl.

11. The trehalose derivative according to claim 10 wherein said three groups are located at 2,3,6'- or 2,6,6,'-positions.

12. The trehalose derivative according to claim 10 wherein said three groups are straight or branched, saturated or unsaturated $C_6$–$C_{36}$ aliphatic acyl group.

13. The trehalose derivative according to claim 10 wherein at least one group of said three groups is substituted with hydroxy, epoxy, alkylcycloalkyl.

14. The trehalose derivative according to claim 1 which is represented by the formula:

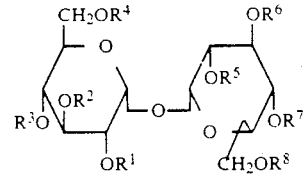

wherein four of $R^1$, $R^2$, $R^3$, $R^4$, $R^5$, $R^6$, $R^7$, and $R^8$ are independently selected from the group consisting of unsubstituted or substituted $C_{1-40}$ aliphatic acyl groups and all the rest of them are hydrogen atoms, with the proviso that said four are not located at corresponding positions with each other or 2,3,4,2'- or 2,3,6,2'-positions.

15. The trehalose derivative according to claim 14 wherein said four groups are located at 2,3,6,6'-positions.

16. The trehalose derivative according to claim 14 wherein said four groups are straight or branched, saturated or unsaturated $C_6$–$C_{36}$ aliphatic acyl group.

17. The trehalose derivative according to claim 14 wherein at least one group of said four groups is substituted with hydroxy.

18. A trehalose derivative of the formula:

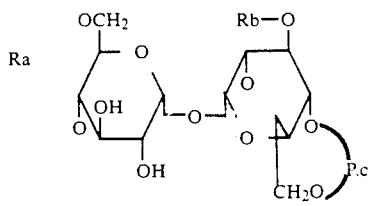
(3)

wherein Ra, Rb and Rc are independently polysiloxanediyl or lower alkylidene which may be substituted with monocyclic aryl.

19. A trehalose derivative of the formula:

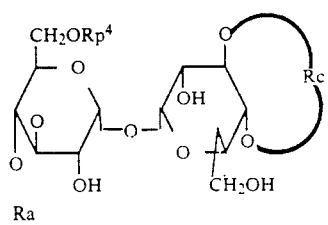
(8)

wherein Ra and Rc are independently polysilanediyl or lower alkylidene which may be substituted with monocyclic aryl; and $R^4p$ is a hydrogen atom or an aryl (lower alkyl) or a tri (lower) alkylsilyl.

* * * * *